(12) United States Patent
Smith

(10) Patent No.: US 8,540,645 B2
(45) Date of Patent: Sep. 24, 2013

(54) NEEDLE BIOPSY DEVICE AND RELATED METHOD

(75) Inventor: Justin Smith, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 174 days.

(21) Appl. No.: 13/192,073

(22) Filed: Jul. 27, 2011

(65) Prior Publication Data

US 2013/0030323 A1    Jan. 31, 2013

(51) Int. Cl.
*A61B 10/00*    (2006.01)

(52) U.S. Cl.
USPC ........................................ 600/564; 600/562

(58) Field of Classification Search
USPC .................................. 600/564; 606/167, 170
See application file for complete search history.

(56) References Cited

U.S. PATENT DOCUMENTS

| | | | |
|---|---|---|---|
| 6,592,530 B1 * | 7/2003 | Farhadi | 600/564 |
| 7,513,877 B2 * | 4/2009 | Viola | 600/564 |
| 7,806,834 B2 * | 10/2010 | Beckman et al. | 600/566 |
| 2004/0138687 A1 * | 7/2004 | Himes | 606/167 |
| 2006/0155210 A1 * | 7/2006 | Beckman et al. | 600/567 |
| 2008/0097505 A1 * | 4/2008 | Kim | 606/189 |
| 2010/0069844 A1 * | 3/2010 | Bonner et al. | 604/117 |

\* cited by examiner

*Primary Examiner* — Jeffrey G Hoekstra
*Assistant Examiner* — Daniel Cerioni
(74) *Attorney, Agent, or Firm* — Vista IP Law Group LLP

(57) ABSTRACT

A needle biopsy device is disclosed. The biopsy device includes a housing, a needle set and an actuator assembly. The needle set includes a needle having a tissue receiving opening and a cutting element adapted to pass over or through the tissue receiving opening to sever tissue extending therein. The actuator assembly includes a first magnetic member fixed in a stationary position in the housing and a second magnetic member arranged in the housing so that the second magnetic member is either magnetically attracted toward or repelled from the first magnetic member. The second member is coupled to a respective one of the needle and cutting member so that movement of the second magnetic member effectuates movement of one of the needle and cutting element.

15 Claims, 20 Drawing Sheets

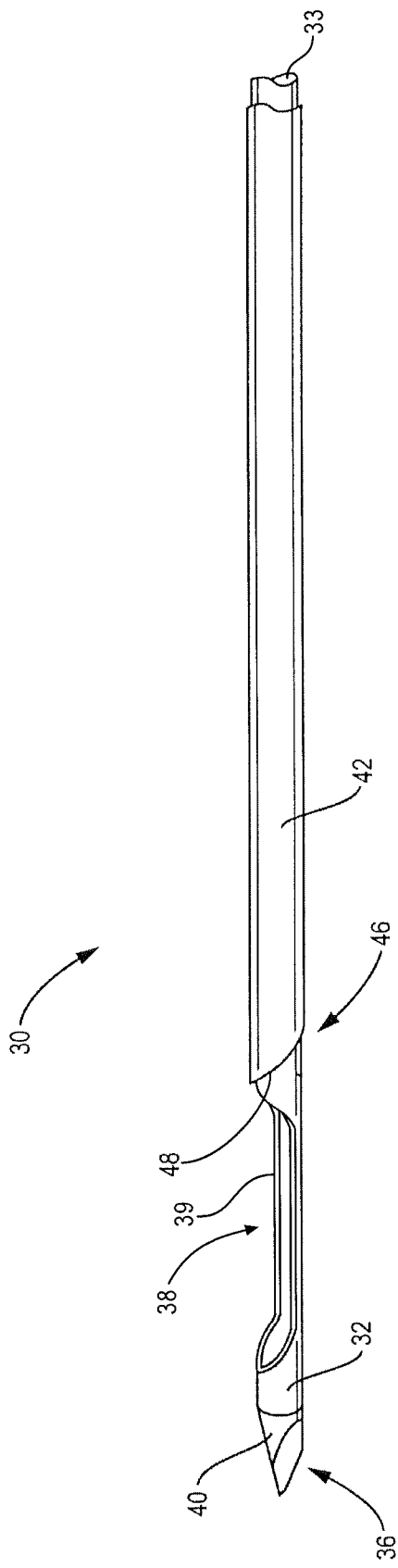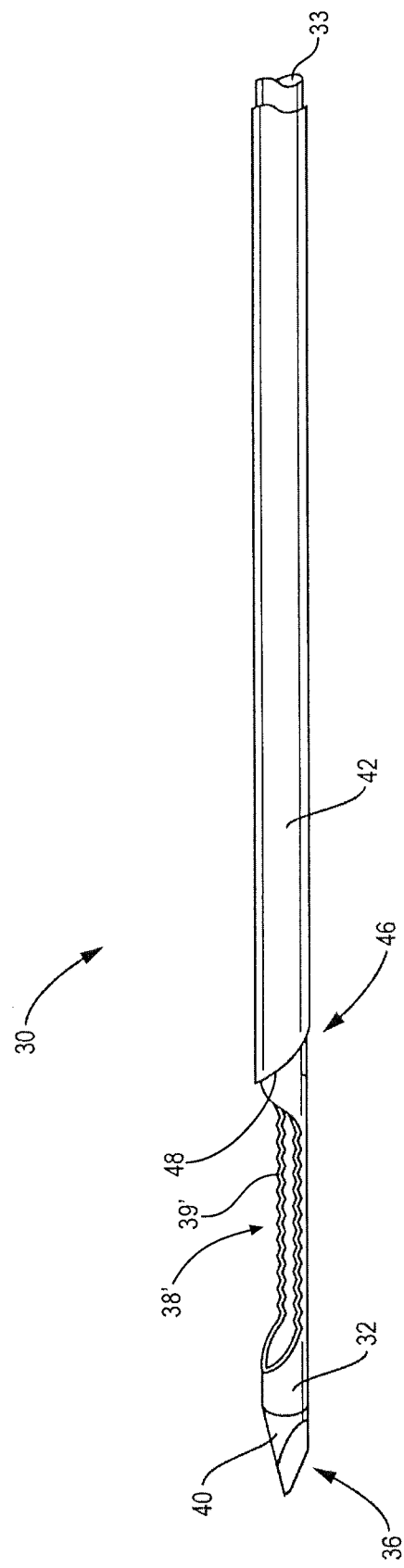

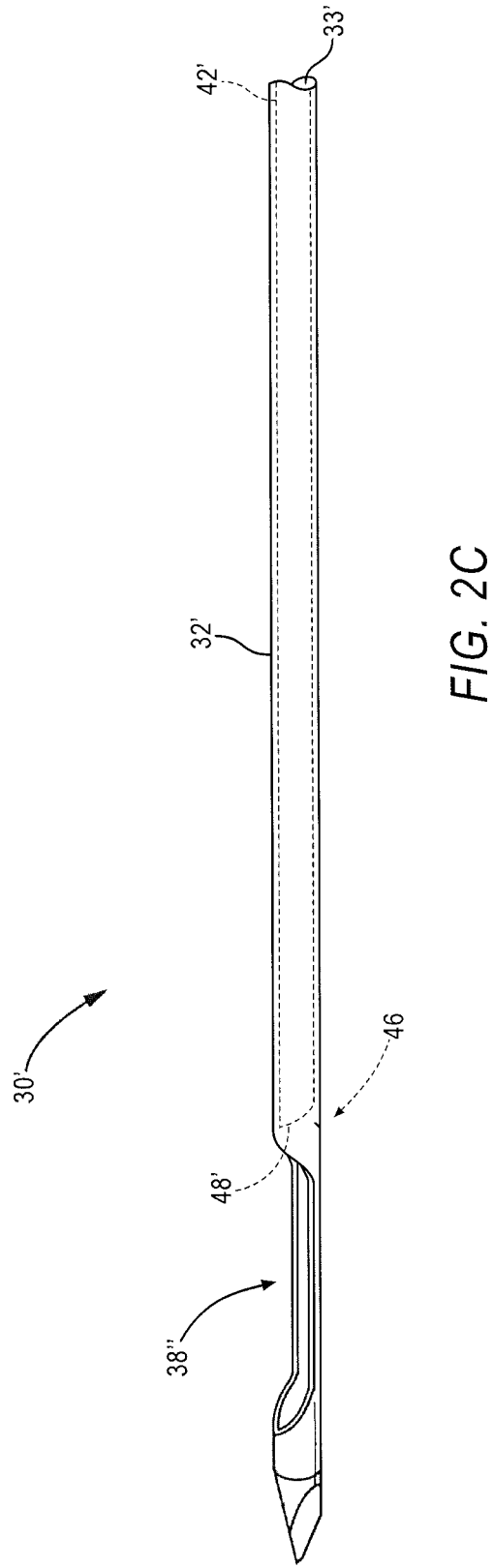

NEEDLE BIOPSY DEVICE AND RELATED METHOD

TECHNICAL FIELD

The present disclosure generally relates to the field of tissue sampling and harvesting for biopsy procedures and, more particularly, to devices and methods for performing needle biopsy procedures.

BACKGROUND

In the practice of diagnostic medicine it is often necessary or desirable to perform a biopsy, or to sample selected tissue from a living patient for medical evaluation. Cytological and histological studies of the biopsy sample can then be performed as an aid to the diagnosis and treatment of disease. For example, biopsies can be particularly useful in diagnosing and treating various forms of cancer, as well as other diseases in which a localized area of affected tissue can be identified.

Biopsies are routinely performed on tissue using motor driven or spring-driven biopsy devices, which employ a working needle set to engage and sever tissue at a targeted tissue site. The needle set typically includes a stylet defining a tissue piercing tip and a tissue receiving opening, and a cutting cannula adapted to cut tissue that is disposed within the tissue receiving opening. In some devices, vacuum is provided to assist in drawing tissue into, as well as maintaining said tissue, within the tissue receiving opening during a cutting operation.

During a typical biopsy procedure, the biopsy device is positioned along a predetermined path that will result in the biopsy device being operatively positioned to reach a target site for performing the biopsy. The stylet is then driven into the tissue and tissue then prolapses into the tissue opening. The cutting cannula is then advanced along the stylet, and over the tissue opening. This forward movement of the cutting cannula operates to sever the prolapsed tissue, thereby obtaining a tissue sample or core, which becomes trapped within the tissue opening of the stylet. With the cutting cannula effectively closing the tissue opening, the biopsy device is then withdrawn from the target site, carrying the sample disposed in tissue opening. To collect the biopsy sample, the cutting cannula is retracted to expose the tissue opening of the stylet, thereby permitting the biopsy sample to be removed from the biopsy device. The procedure may be repeated several times until satisfactory samples have been obtained.

SUMMARY

In one aspect, the present disclosure is directed to a biopsy device. In certain embodiments, the biopsy device comprises a housing, a needle set mounted to the housing, and an actuator assembly. The needle set includes a needle defined by a proximal end, a distal end and at least one tissue-receiving opening. The needle is selectively movable relative to the housing between retracted and extended positions. The needle set further includes a cutting element defined by a proximal end, an open distal end and a cutting edge. The cutting element is selectively moveable relative to the housing between retracted and extended positions and operable to sever tissue projecting into the at least one tissue-receiving opening.

The actuator assembly includes a first magnetic member fixed in a stationary position in the housing and a second magnetic member arranged in the housing. The second magnetic member is coupled to one of the needle and cutting element. The second magnetic member is configured to be either repelled or attracted to the first magnetic member so as to move the second magnetic member from a first retracted position to a second extended position, thereby effectuating movement of the coupled needle or cutting element from its retracted position toward its extended position.

BRIEF DESCRIPTION OF DRAWINGS

Details of one or more exemplary implementations of the disclosure are set forth in the accompanying drawings and in the description below. Further features, aspects, and advantages will become apparent from the description, the drawings, and the claims.

FIG. 2A is an enlarged perspective view of a distal end of a needle set of the device of FIG. 1.

FIG. 2B is an enlarged perspective view of an alternative embodiment of the distal end of the needle set of the device of FIG. 1.

FIG. 2C is an enlarged perspective view of the distal end of an alternative arrangement of a needle set that may be used with the device of FIG. 1.

Although the drawings represent exemplary embodiments of the present disclosure, the drawings are not necessarily to scale and certain features may be exaggerated in order to better illustrate and explain features of various exemplary configurations of the disclosure. The exemplification set out herein illustrates only exemplary embodiments of the disclosure, in one, or more forms, and such exemplifications are not to be construed as limiting the scope of the disclosure in any manner.

DETAILED DESCRIPTION

Figure 1:
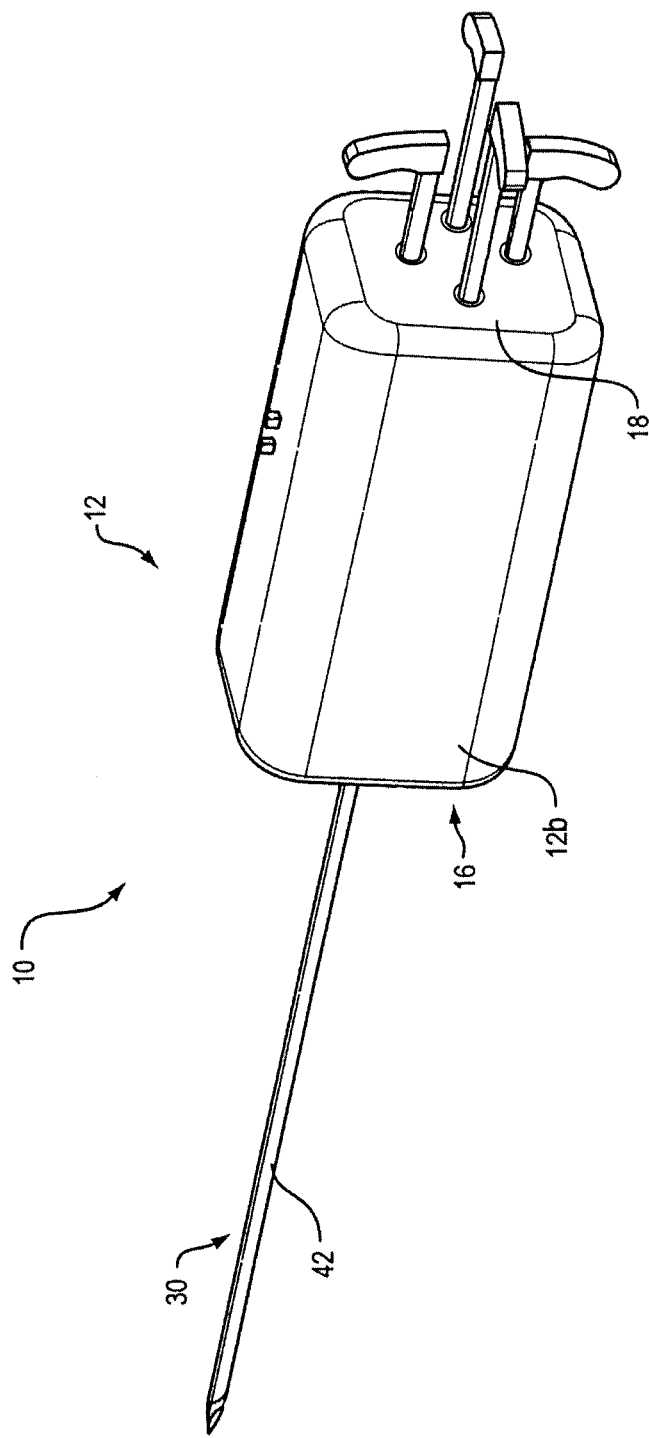
FIG. 1 is a perspective view of an exemplary needle biopsy device.

Referring to FIGS. 1-2 an exemplary configuration of a biopsy device is indicated generally by the reference numeral 10. Biopsy device 10 advantageously offers a cost effective and less complicated arrangement for driving and actuating the components of biopsy device 10 to retrieve viable tissue samples. In one exemplary configuration, biopsy device 10 comprises a housing 12, a needle set 30 and an actuator assembly (best seen in FIGS. 3A-3C) positioned within housing 12.

The housing 12 is defined by a proximal end 14 and a distal end 16, and in one exemplary arrangement, may be formed as a two piece component including a first housing member 12a (see, e.g., FIG. 3A) and a second housing member 12b (seen in FIG. 1). For example, in one exemplary embodiment, first and second housing members 12a and 12b are configured to mate together, such as, for example, in a snap-fit engagement, to house and positionally support components of the actuator assembly. While the housing 12 has been described as mating together in a snap-fit arrangement, it is also understood that the first and second housing members 12a and 12b may alternatively be secured together, for example, by using fastening hardware (e.g. screws) and/or adhesives, and/or by employing other fastening technique known to those of ordinary skill in the art. Further, the housing 12 may be alternatively configured. For example, the housing 12 could be formed from more than two housing members or could be formed primarily from a single housing member defining an access opening covered by a movable door (i.e. an opening and closing door) or a releasably secured door (i.e. an attachable and removable door).

In the exemplary embodiment shown in the FIGS., the housing 12 is further defined by a distal wall 13, a proximal wall 18, and two opposing side walls. The distal wall 13 further includes a distal aperture (element 15 shown in FIG. 4A, for example) through which the needle set 30 passes. The proximal wall 18 further includes one or more proximal apertures 20a, 20b, through which first and second manually engageable actuator members 60, 62 extend. First and second engageable actuator members are discussed in further detail below in connection with FIGS. 4A-4D.

Although the housing 12 is illustrated throughout the figures as being generally configured as an elongated rectangular body having an approximately square cross-section with rounded edges, it should be noted that the housing 12 can take on any of numerous shapes and configurations. For example, the housing 12 could have a cylindrical configuration or an asymmetrical configuration formed from a combination of straight, curved and/or curvilinear surfaces, and the cross section could be consistent throughout or it could vary at different points along the longitudinal axis. Hence, the shape and cross-sectional geometry of the housing 12 should not be interpreted in a limiting sense.

Referring to FIGS. 2A-2B, exemplary embodiments of the needle set 30 are shown in further detail. Generally, the needle set 30 comprises an elongated stylet or needle 32 defined by a proximal end 34 (best seen in FIGS. 3A-3B), a distal end 36 and at least one tissue receiving opening 38/38' disposed at or adjacent the distal end 36. In one exemplary arrangement, as seen in FIG. 2A, the tissue receiving opening 38 is defined by a generally continuous smooth edge 39. Alternatively, as seen in FIG. 2B, the tissue receiving opening 38' is defined by a serrated edge 39.'

The needle 32 is configured to be selectively movable relative to the housing 12 between a first retracted/armed position and a second extended/fired position, as will be explained in further detail below. In one exemplary arrangement, the needle 32 may further include a tissue piercing tip 40, such as the trocar tip illustrated throughout the figures. However, it should be noted that the tip 40 may take on any of numerous configurations known to those of ordinary skill in the art. For example, the tip 40 may include one or more sharpened protrusions or blades extending from one or more surfaces of the distal end 36. Also, the tip 40 could include any number of facets, or could take the form of a single faceted conical tip. Still further, the tip 40 could be configured as a blunt tip for applications where the lesion to be biopsied is close to the chest wall such that it is desirous to avoid excessive tissue-piercing. The needle 32 may be provided in any desired size. For example, needle 32 may be sized within the range of 6-18 gauge. In one particular exemplary embodiment, the needle 32 is a 9 gauge needle and in an alternative exemplary embodiment the needle 32 is a 12 gauge needle. However, it should be noted that the needle 32 can be of any known gauge size suitable for performing any particular biopsy procedure.

In one exemplary embodiment, the proximal end 34 of the needle 32 is configured with an open proximal end. Further, the needle 32 also defines a lumen 33 extending from the tissue receiving opening 38/38' to the open proximal end 34.

The needle set 30 further comprises an elongate cutting element 42 defined by a proximal end 44 (best seen in FIGS. 3A-3B), an open distal end 46. A cutting edge 48 is formed on the open distal end 46, and a lumen (not shown) extends at least partially from the cutting edge toward the proximal end 44. In one embodiment, the cutting element 42 is configured as an elongate cannula having a substantially cylindrical profile, however the cannula may take on alternative profiles, for example an elliptical or octagonal profile. The cutting element 42 is configured to be selectively moveable relative to the housing 12 (and needle 32) between a first retracted/armed position and a second extended/fired position (as will be discussed in further detail below), and is operable to sever tissue that prolapses into the at least one tissue-receiving opening 38/38' in the needle 32.

In the illustrated embodiment, the cutting element 42 is disposed over the needle 32 in a sliding relationship, so that the needle 32 and cutting element 42 are able to move axially relative to each other and the cutting element 32 is able to pass over the tissue-receiving opening 38 when moving from its retracted position toward its extended position to sever tissue prolapsed into the tissue-receiving opening 38.

In an alternative embodiment shown in FIG. 2C, the needle set 30' may be configured such that the needle 32' is sized and configured to be disposed over the cutting element 42' in a sliding relationship. In this arrangement, the needle 32' and cutting element 42' are also able to slide axially relative to each other. More specifically, the distal end 46' of the cutting element 42' is shown retracted away from the tissue receiving opening 38" of the needle 32' such that tissue is able to prolapse into the tissue-receiving opening 38'. Cutting element 42' is then moved within lumen 33' from its retracted position toward an extended position such that cutting edge 48' severs the tissue that has prolapsed into the tissue-receiving opening 38'.

In either embodiment, the needle 32/32' and the cutting element 42/42' may be coaxially positioned relative to each other or may be eccentrically positioned relative to each other, so long as the needle 32/32' and cutting element 42/42' maintain their sliding relationship.

Figure 3A:
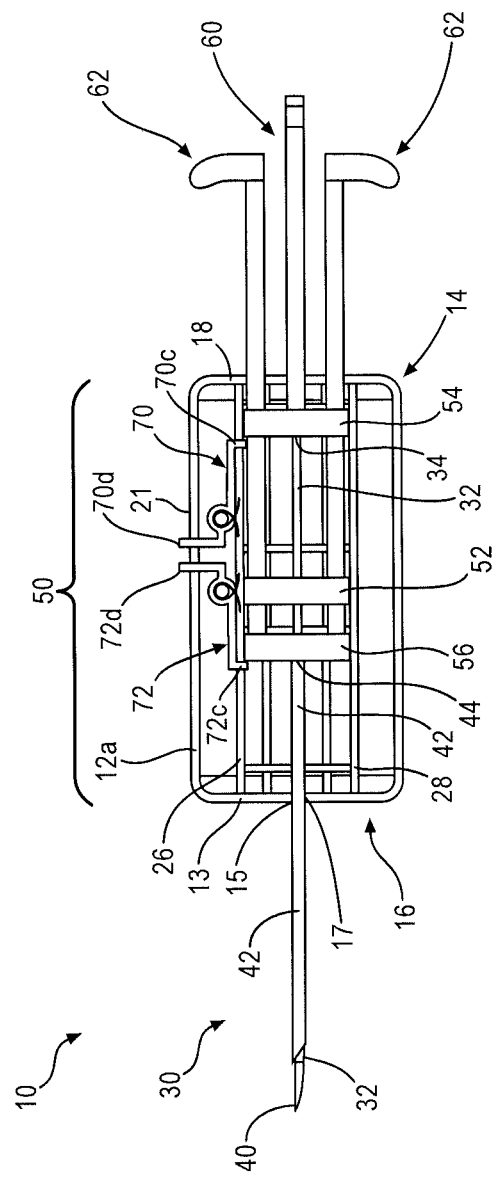
FIG. 3A is a side elevational view of the device of FIG. 1 with a portion of the housing removed; wherein the device of FIG. 1 is in a retracted position.
Figure 3B:
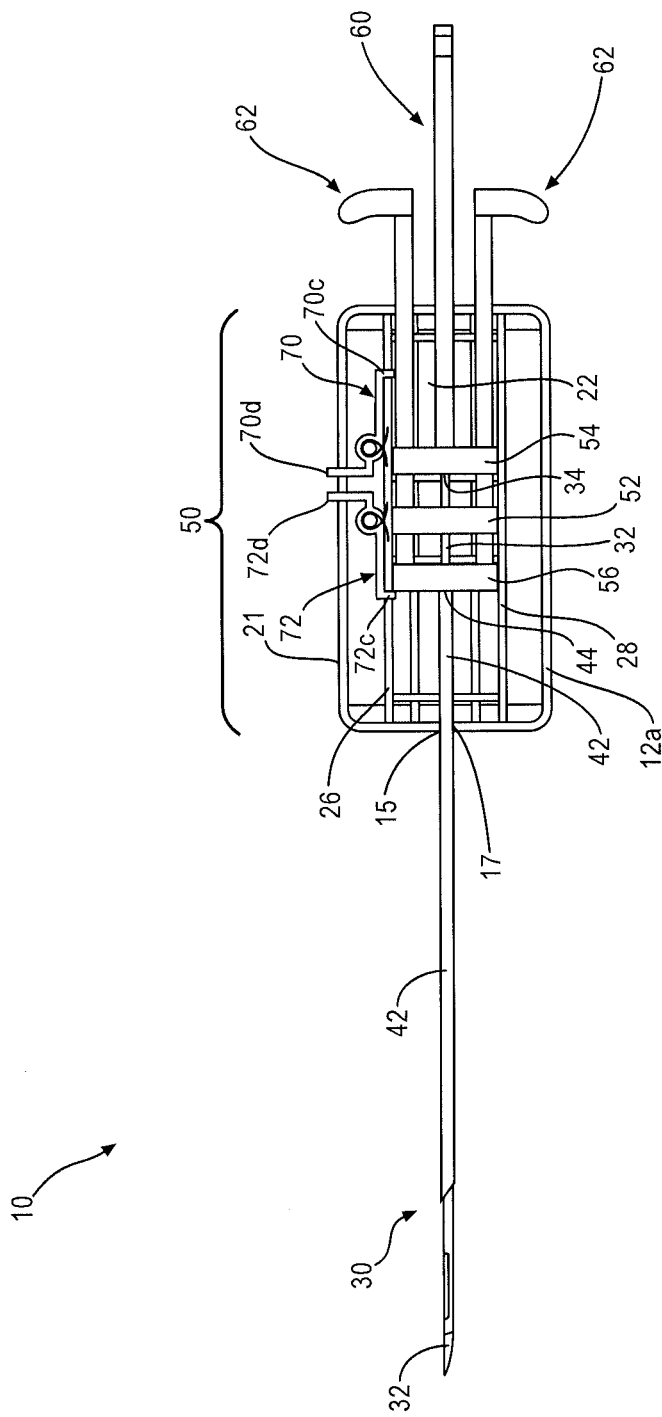
FIG. 3B is a side elevational view of the device of FIG. 3A, after an inner cannula has been moved to a fired position.
Figure 3C:
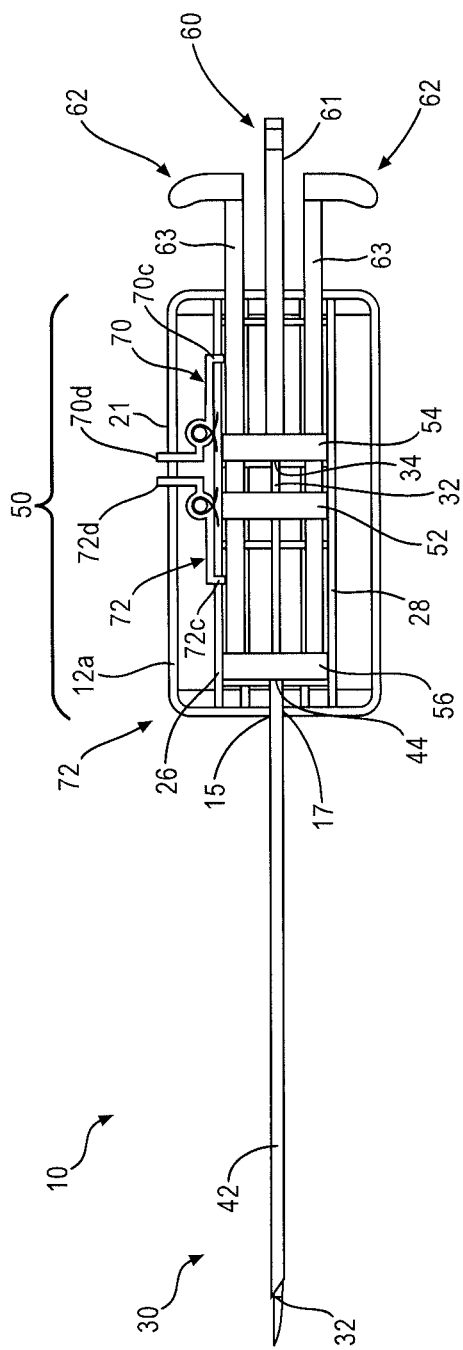
FIG. 3C is a side elevational view of the device of FIGS. 3A-3B, after an outer cannula has been moved to a fired position.

Turning to FIGS. 3A-C, a cross-sectional view of the exemplary biopsy device 10 is illustrated. For clarity, second housing member 12b is removed such that the exemplary configuration of an actuator assembly 50 may be seen in further detail. The various positions of the components of actuator assembly 50 are illustrated in FIGS. 3A-3C, and shall be described in further detail. In one exemplary arrangement, the actuator assembly 50 comprises a first magnetic member 52, a second magnetic member 54 and a third magnetic member 56. The first magnetic member 52 is positioned between the second and third magnetic members 54 and 56 and is fixed with respect to the housing 12 (first housing member 12a being visible in this view). The second magnetic member 54 is arranged in the housing 12 so that second magnetic member 54 is selectively movable and magnetically attracted toward the first magnetic member 52 in a first direction (i.e., in the distal direction) from a first (retracted) position (See, e.g. FIG. 3A) toward a second (extended) position (See, e.g. FIG. 3B). The third magnetic member 56 is arranged in the housing 12 so that the third magnetic member 56 is selectively movable and magnetically repelled away from the first magnetic member 52 in a first direction (i.e., in the distal direction) from a first (retracted) position (See, e.g. FIG. 3A) toward a second (extended) position (See, e.g. FIG. 3C).

As may be seen, in the illustrated embodiment, the second magnetic member 54 is proximally located in the housing 12 relative to the first magnetic member 52 and the third magnetic member 56 is distally located in the housing 12 relative to the first magnetic member 52. However, as recognized by those of ordinary skill in the art, the location and/or orientation of the magnetic members 52, 54, 56 may be altered. For example, the positions of second 54 and third magnetic 56 members could be swapped so that the second magnetic member 54 is distally located in the housing 12 and the third magnetic member 56 is proximally located within the housing 12. Alternatively, the second and third members 54, 56 could both be arranged proximally in the housing 12 relative to the first magnetic member 52 so that the second magnetic member 54 is attracted toward the first magnetic member 52 and the third magnetic member 56 is attracted toward the second magnetic member 54. As another example, the second and third members 54, 56 could both be arranged in the housing 12 distally relative to the first magnetic member 52 so that the second magnetic member 54 is repelled by the first magnetic member 52 and the third magnetic member 56 is repelled by the second magnetic member 54. It should be noted that in the latter two examples, the positions of the second and third magnetic members 54, 56 could be swapped so that the third magnetic member 56 is attracted toward or repelled by the first magnetic member 52 and the second magnetic member 54 is attracted toward or repelled by the third magnetic member 56. Hence, the location of the magnetic members 52, 54, 56 is not limited to the specific embodiments illustrated in the various FIGS.

The housing 12 may further be configured with internal support surfaces for supporting the magnetic members 52, 54, 56 within the housing 12, and serving as travel platforms upon which the second and third magnetic members 54, 56 travel/slide when moving between their respective first retracted and second extended positions. In the exemplary arrangement depicted in FIGS. 3A-3C, the housing 12 includes at least one upper support surface 26 and at least one lower support surface 28. In one exemplary arrangement, both support surfaces 26, 28 are configured to extend substantially the length of the housing 12. More specifically, the support surfaces 26, 28 extend laterally in a cantilevered manner from at least one side wall of the housing 12 in a direction transverse to the longitudinal axis of the housing 12. In the illustrated exemplary embodiment, the upper and lower support surfaces 26, 28 are configured as single continuous surfaces which extend from a common side wall. However, it should be noted multiple configurations are possible, without departing from the disclosure. For example, the upper support surface 26 may extend from one side wall and the lower support surface 28 may extend from the opposite side wall. Still further, the support may comprise separate components (as opposed to being one continuous component), i.e., the upper support surface 26 and the lower support surface 28 could each be configured as a single support surface section extending from one side wall and a second opposing surface section extending from an opposite side wall. In this latter exemplary configuration, the separate support surfaces could abut each other, or, if desired, a gap of a predetermined length could reside between opposing support surfaces.

Figure 13:
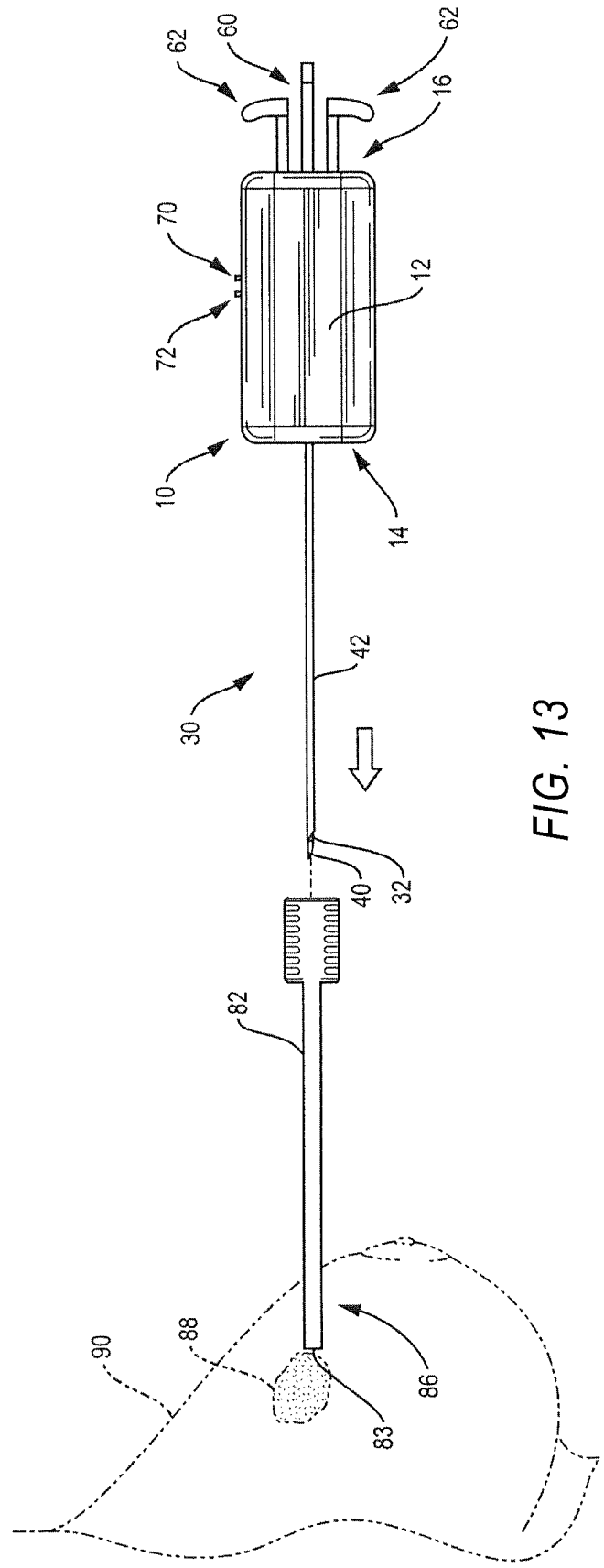
FIG. 13 is a side view of the introducer-stylet assembly of FIG. 12 with the device of FIG. 1 being inserted into the introducer sheath.
Figure 14:
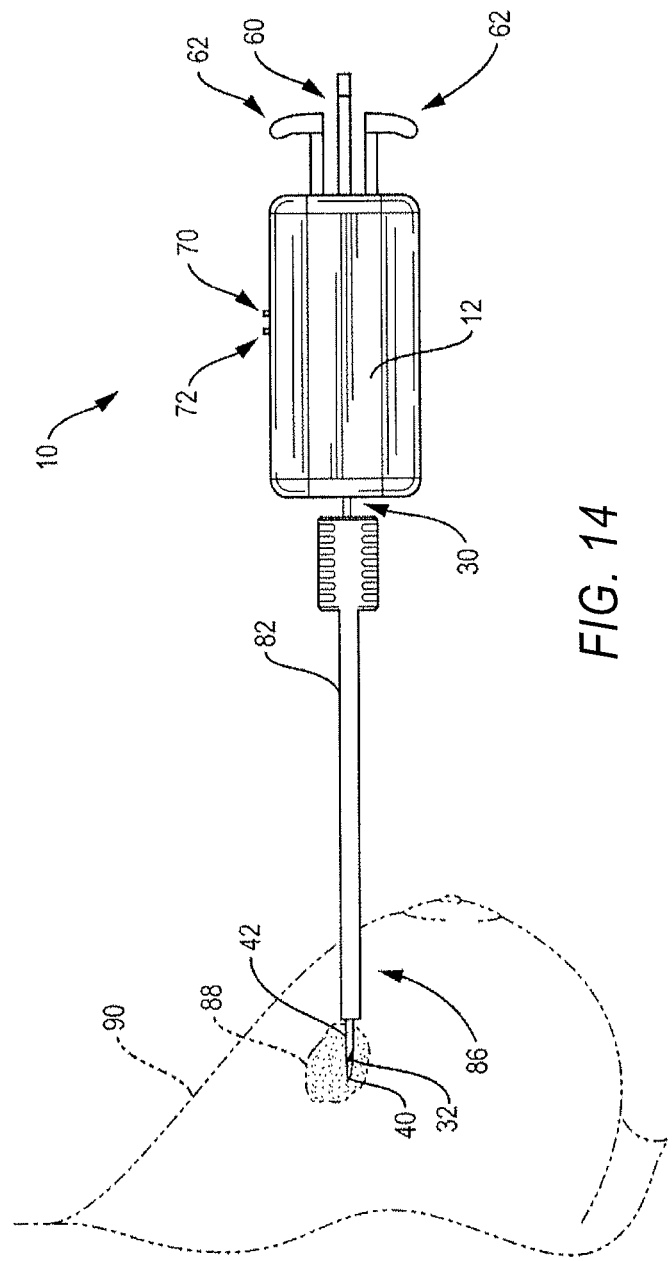
FIG. 14 is a side view of the introducer-stylet assembly of FIG. 13 with the device of FIG. 1 inserted into the introducer sheath and extending to the target tissue site.

To effectuate movement of (i.e. drive forward and retract) the needle 32/32' and cutting element 42/42' between their respective retracted and extended positions, the second and third magnetic members 54, 56 are respectively coupled to one of the needle 32/32' and cutting element 42/42' in such a manner such that when the second and third magnetic members 54, 56 move, the needle 32/32' and cutting element 42/42' also move. For example, in the illustrated exemplary embodiment, the second magnetic member 54 is coupled to a portion of the needle 32/32' and the third magnetic member 56 is coupled to a portion of the cutting element 42/42'. In this exemplary configuration, movement of the second magnetic member 54 from a first retracted position (FIGS. 3A-3B) toward a second extended position (FIG. 3C) moves the needle 32/32' from its retracted position (FIG. 3A) toward its extended position (FIG. 3B) (i.e. drives the needle forward to pierce tissue, as will be explained in further detail below in connection with FIG. 13)). Movement of the third magnetic member 56 from its first retracted position (FIG. 3A) toward its second extended position (FIG. 3C) moves the cutting element 42/42' from its retracted position toward its extended position (i.e. drives the cutting element forward to cut tissue, as will be explained in further detail below in connection with FIG. 14). Of course, the opposite is true as well—i.e. movement of the second magnetic member 54 from its second extended position toward its first retracted position moves the needle 32/32' from its extended position toward its retracted position (i.e. retracts the needle 32/32'), and movement of the third magnetic member 54 from its second extended position toward its first retracted position moves the cutting element 42/42' from its extended position toward its retracted position (i.e. retracts the cutting element). Although the second magnetic member 54 is shown coupled to the needle 32/32' and the third magnetic member 56 is shown coupled to the cutting element 42/42', it should be noted that the second magnetic member 54 could be coupled to the cutting element 42/42' and the third magnetic member 56 could be coupled to the needle 32/32' if so desired.

As appreciated by those skilled in the art, the second and third magnetic members 54, 56 can be coupled to the needle 32/32' and cutting element 42/42' by a myriad of known coupling techniques. For example, in the illustrated embodiment, the second and third magnetic members 54, 56 each may include apertures, each such aperture receiving one of the needle 32/32' and cutting element 42/42' in an interference or frictional relationship (i.e. a portion of the needle and cutting element is press fit into a respective aperture of one of the second and third magnetic members 54, 56 creating an interference or frictional fit operable to prevent decoupling). Alternatively, the needle 32/32' and cutting element 42/42' could be welded, brazed, soldered or otherwise fixedly joined to a respective magnetic member by an alternative joining technique, or coupled to a respective magnetic member by way of an adhesive, mechanical coupling or fastener. Hence, a variety of coupling techniques may be employed without departing from the claimed invention.

The first 52, second 54 and third 56 magnetic members are wholly or in part permanent magnets formed from a magnetic material, alloy or composition. Exemplary permanent magnets include, but are not limited to, rare earth magnets, such as Neodymium magnets (Neodymium-Iron-Boron; NdFeB) and Samarium-Cobalt magnets (SmCo) and non-rare earth magnets, such as Alnico magnets (Aluminum-Nickel-Cobalt; AlNiCo) and ceramic (ferrite) magnets. It is further contemplated that one or more of the magnetic members could be electromagnets, in which case the device 10 would include an electrical current source (not shown) or be adapted to connect to an external electrical current source (not shown). In the illustrated embodiment, the magnetic members 52, 54, 56 are depicted as having a substantially square configuration; however, the magnetic members 52, 54, 56 may have any of numerous alternative configurations known to those of ordinary skill in the art including, but not limited to, rectangular, disk, cylindrical and ring configurations. In one exemplary embodiment, the magnetic members are square Neodymium magnets approximately 1 inch in length, approximately 1 inch in width and approximately ½ inch thick. However, it should be noted that said dimensions are not absolute and may vary as desired; for example, the length and width dimensions may range from about ½ inch to about 2 inches and the width may range from about ⅛ inch to about 1 inch.

With continued reference to FIGS. 3A-3C, additional components of the actuator assembly 50 will be described. Actuator assembly 50 further comprises a first manually engageable actuator member 60 operatively coupled to the second magnetic member 54 and a second manually engageable actuator member 62 operatively coupled to the third magnetic member 56. The engageable members 60 and 62 are coupled or otherwise attached directly or indirectly to respective magnetic members 54 and 56 in a similar fashion as discussed above with respect to the coupling of the magnetic members to the needle 32/32' and cutting element 42/42'. The engageable actuator members 60 and 62 effectuate selective movements of the second and third magnetic members 54, 56 along a longitudinal axis of the device 10. In the illustrated exemplary embodiment, the first manual engageable actuator member 60 operates to selectively return the second magnetic member 54 from its second extended position (See, e.g. FIG. 3C) to its first retracted position (See, e.g. FIG. 3A-3B) in a second proximal direction along the longitudinal axis of the device 10, i.e., a direction that is away from the first magnetic member 52. In other words, the first actuator member 60 returns needle 32/32' to its retracted position.

The second manually engageable actuator member 62, on the other hand, effectuates selective movement of the third magnetic member 56 from its second extended position (See, e.g. FIG. 3C) to its first retracted position (See, e.g. FIG. 3A) in the proximal direction along the longitudinal axis of the device 10 that is toward the first magnetic member 52. Thus, second manually actuator member 62 returns cutting element 42/42' to its retracted position.

Figure 4A:
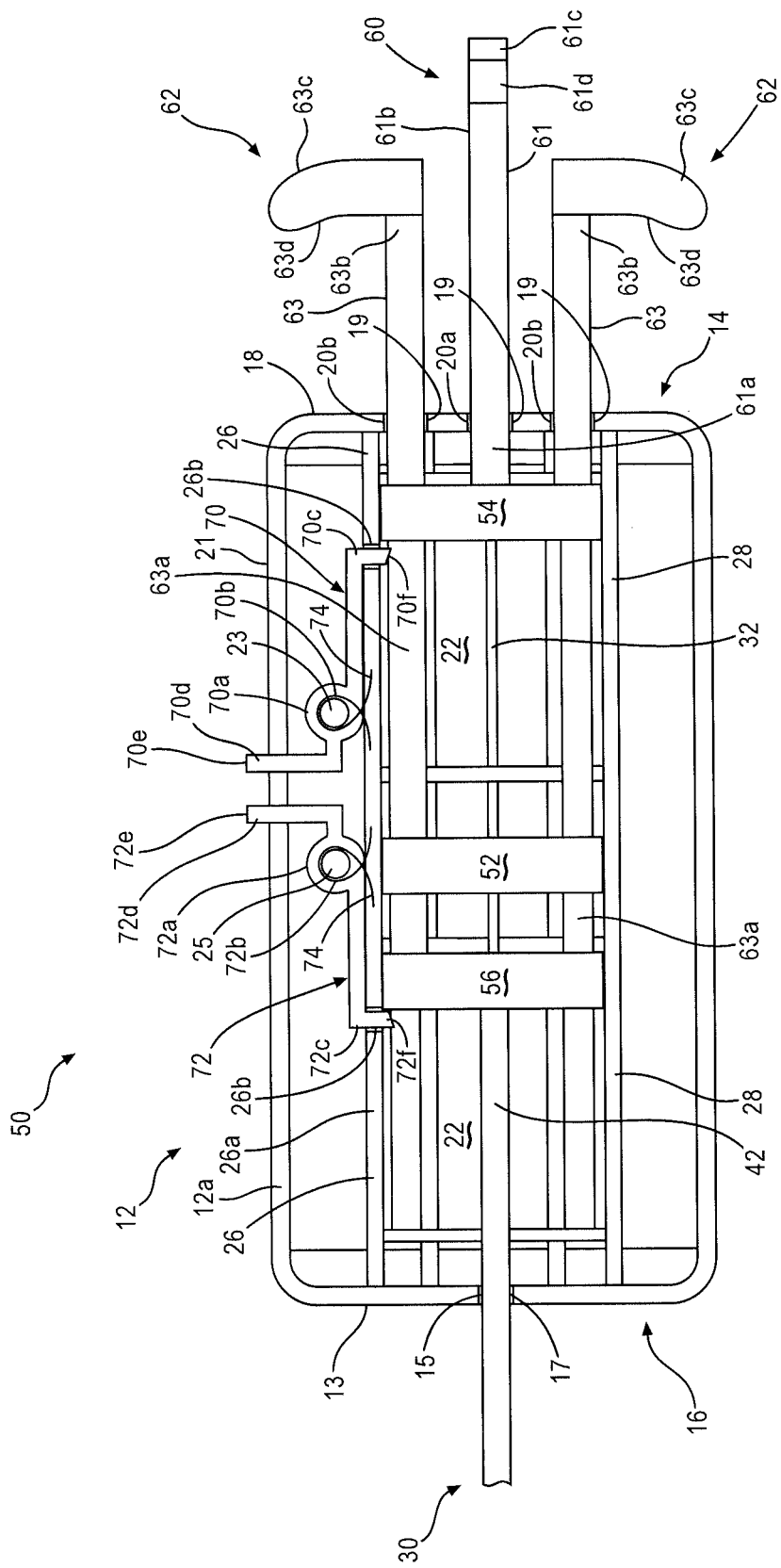
FIG. 4A is an enlarged sectional view of the housing and an actuator mechanism of the device shown in FIG. 3A, with the device in the retracted position.
Figure 4C:
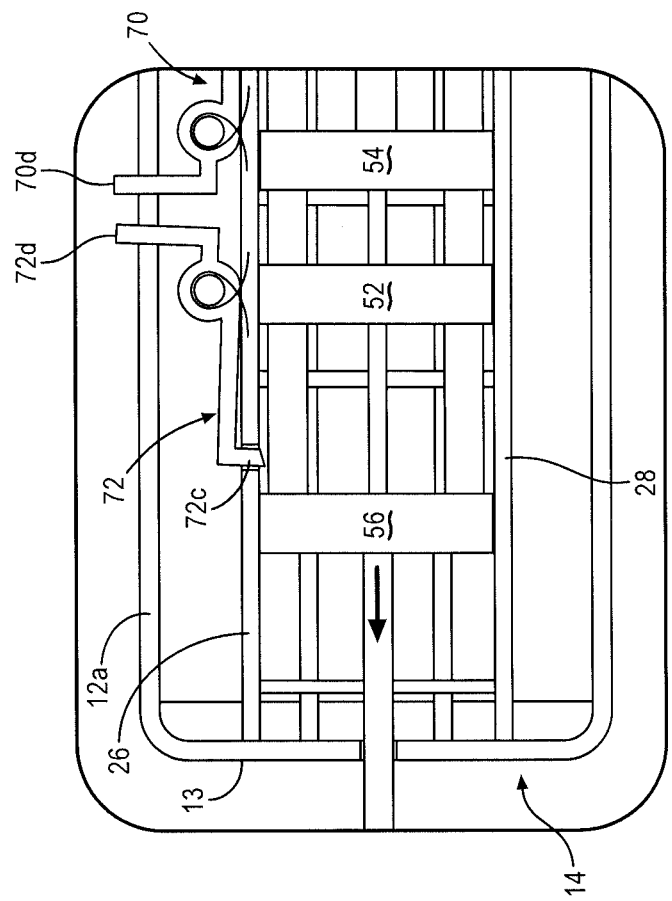
FIG. 4C is an enlarged sectional view illustrating the operation of a second magnetic member of the actuator mechanism.
Figure 4B:
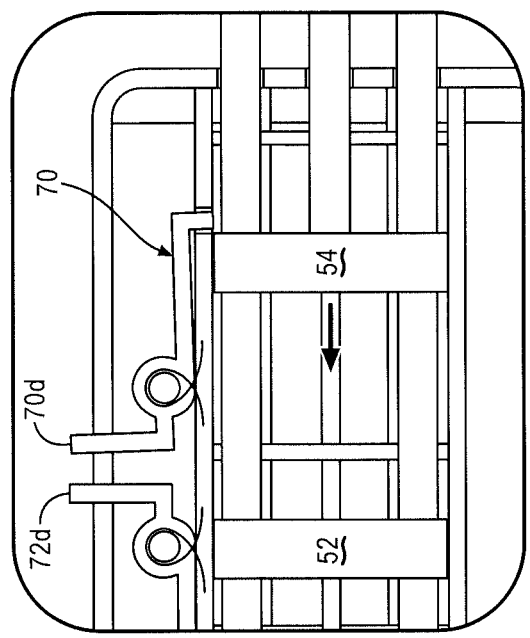
FIG. 4B is an enlarged sectional view illustrating the operation of a first magnetic member of the actuator mechanism.

Details of the first and second engageable actuator mechanisms 60, 62 may be seen in FIGS. 4A-4B. First and second engageable actuator mechanisms 60, 62 each include at least one elongate shaft 61, 63, with each shaft having distal ends 61a, 63a, which are positioned within the housing 12, and proximal ends 61b, 63b, which protrude at least partially from the proximal end 14 of the housing 12. In the illustrated exemplary embodiment, the shafts 61b, 63b are generally cylindrically shaped, however, it should be noted that the shafts can take on any of numerous configurations known to those skilled in the art; for example, the shafts 61b, 63b could take on a square or hexagonal configuration. Handles 61c, 63c extend from the proximal ends 61b, 63b of each shaft. In one exemplary arrangement, the shafts 61, 63 are integrated with the handles 61c, 63c, such that the shafts 61, 63 and handles 61c, 63c form one-piece components; however, the shafts 61, 63 and handles 61a, 63a can be separately formed components attached together at the proximal end of the shaft, thus forming a two-piece component. In one exemplary embodiment, the handles 61c, 63c may be configured to define a concave indentation 61d, 63d ergonomically configured to receive a portion of a user's finger, which is particularly useful when retracting the second and third magnetic members 54, 56 from their respective extended positions, to their respective retracted positions to, in turn, arm the device 10 for a biopsy procedure. As recognized by one skilled in the art, the handles 61c, 63c can take on any of numerous alternative configurations suitable for allowing the user to engage the manually engageable members 60, 62 to arm the device 10.

Figure 4D:
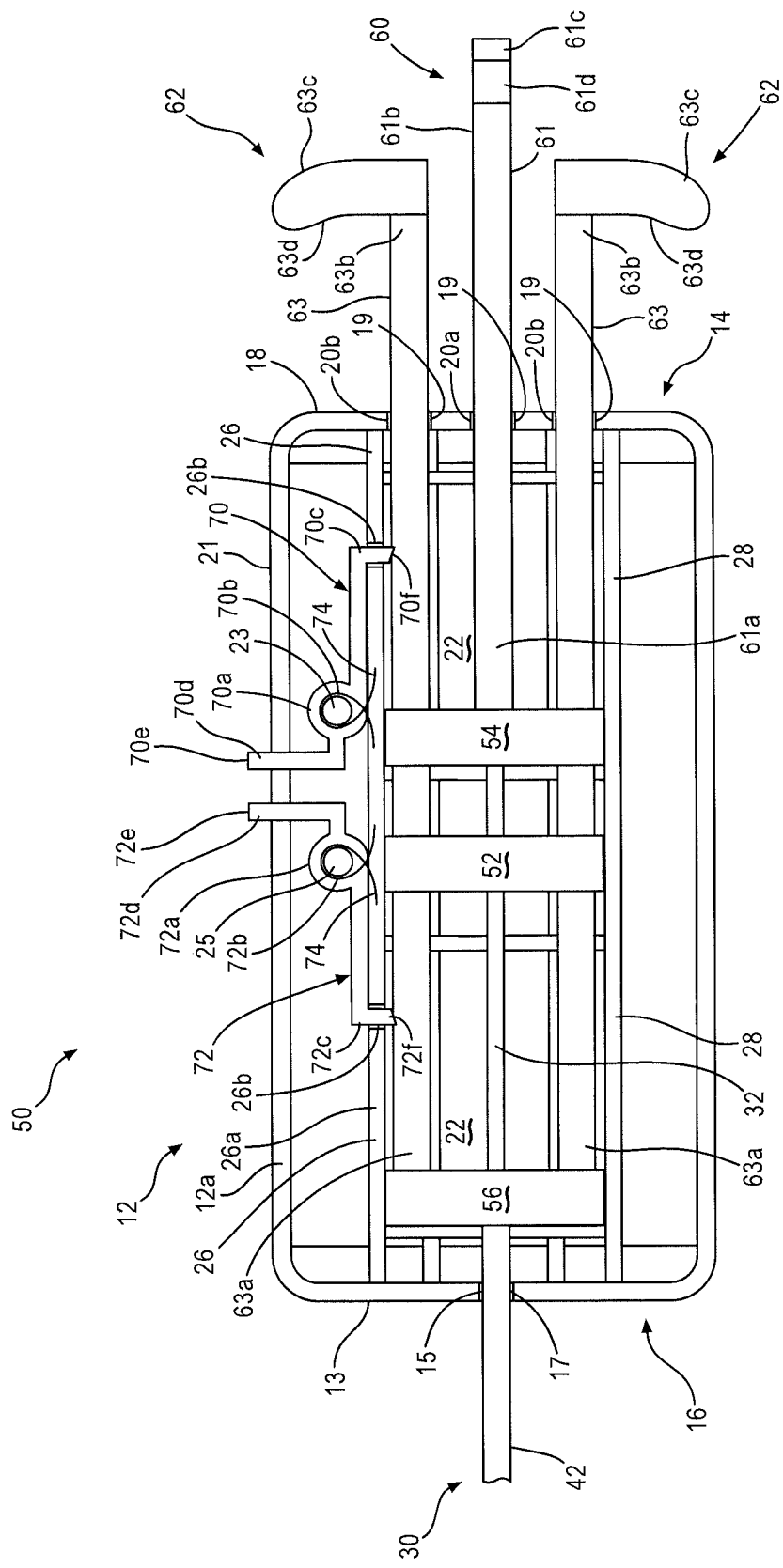
FIG. 4D is an enlarged sectional view of the housing and actuator mechanism of the device shown in FIG. 3C, with the device in the fully fired position.

With attention drawn to FIGS. 4A-4D, in the illustrated, exemplary embodiment, the actuator assembly 50 further includes a first firing member 70 that is configured to be selectively movable between a holding position (See FIG. 4A) and a firing position (FIG. 4C) and a second firing member 72 that is also configured to be selectively movable between a holding position (FIG. 4A) and a firing position (FIG. 4D). The firing members 70, 72 are configured to release the needle 32/32' and cutting element 42/42', respectively. Details of the holding positions and firing positions for the first and second firing members 70 and 72 will be explained in further detail below.

In one embodiment, a biasing member 74, such as, for example, a torsion spring, is mechanically coupled to the housing 12 and to each firing member 70, 72 to bias each firing member toward its respective holding position. As recognized by those of ordinary skill in the art, in addition to torsion springs, the biasing member 74 can be any of numerous types of springs such as, for example, coil springs (constant or variable pitch) or leaf springs. Further, it is contemplated that other known biasing members including, but not limited to, rubber, elastic or elastomeric biasing members could be used in place of springs. Hence, the type of biasing member utilized should not be interpreted in a limiting sense.

The firing members 70, 72 are each attached internally within the housing 12 in a pivoting configuration. More specifically, as demonstrated in FIGS. 4B and 4C, the firing members 70, 72 each pivot about a point within the housing 12 between holding and firing positions. In one embodiment, the housing 12 includes a pair of axially extending cylindrical protrusions 23, 25, which are laterally spaced relative to each other within the housing 12 and extend from an internal side wall 22 of the housing 12, such that the axis of each protrusion is approximately transverse to the longitudinal axis of the housing 12. As appreciated by one skilled in the art, the protrusions 23, 25 could extend form any internal surface or wall of the housing 12 as long the protrusions can serve as axles upon which the firing members 70, 72 may pivot. The firing members 70, 72 each further include a hub 70a, 72a, which defines a receiving aperture 70b, 72b configured to receive a respective cylindrical protrusion 23, 25. The mechanical interaction between the cylindrical protrusions 23, 25 and the receiving apertures 70b, 72b is devised so that the firing members 70, 72 pivot about the axes of the cylindrical protrusions 23, 25.

In the exemplary embodiments, each firing member 70, 72 further includes a holding portion 70c, 72c at one end, which extend toward a central longitudinal axis of the housing 12, and a manually engageable portion 70d, 72d at its opposite end, which extends away from the central longitudinal axis of the housing 12. The manually engageable portions 70d, 72d are configured to extend through respective openings in the housing 12 to an external location beyond an outer surface 21 of the housing 12. Having this configuration, the respective outboard ends 70e, 72e of the manually engageable portions 70d, 72d can be depressed or otherwise engaged or actuated to selectively pivot the firing members 70, 72 between their respective holding and firing positions. It is understood, however, that the present disclosure is not limited the particular firing member 70, 72 arrangements disclosed herein. Indeed, other mechanisms capable of restraining and releasing the needle 32/32' and cutting element 42/42' from their respective retracted positions may be used in place of firing members 70, 72.

In certain exemplary embodiments, the firing member holding portions 70c, 72c are configured so that they extend axially through corresponding apertures or slots 26a, 26b in an internal surface of the housing (described in further detail below) such that when the firing members 70, 72 are in their respective holding positions, as shown in FIG. 4A, the second and third magnetic members 54, 56 are restrained from moving from their first, retracted positions. When the firing members 70, 72 are actuated into their firing positions, the firing member holding portions 70c, 72c are pivoted so as to retract at least partially upward into the slots 26a, 26b, as shown in FIGS. 4B and 4C, respectively. Further, in some exemplary embodiments, the outboard ends 70f and 72f of the holding portions 70c, 72c are configured so as to be angled (they could also curved or angled and curved). For example, in one exemplary arrangement, outboard end 72f is angled in an upward direction moving from the proximal end 14 of the housing 12 towards the distal end 16 of the housing 12. In operation, the second magnetic member 54 is able to move from its retracted position (See, e.g. FIG. 4A) to its extended position (See, e.g. FIG. 4D) without interference from the holding portion 70c, as the firing member 70 is actuated (i.e. the holding portion 70c will pivot into the slot 26a when contacted, and second magnetic member 54 will be attracted to the first magnetic member 52 such that the second magnetic member will travel from its retracted position to its extended position). Similarly, outboard end 72f may also be angled (or curved or angled and curved) in an upward direction moving from the distal end 16 of the housing 12 to the proximal end 14 of the housing 12. In operation, the third magnetic member 56 is able to move from its retracted position (See, e.g., FIG. 4A) to its extended position (See, e.g., FIG. 4D) without interference from the holding portion 72c, as the firing member 72 is actuated (i.e., the holding potion 72c will pivot up into the slot 26b when contacted, and the third magnetic member 56 will be repelled from the first magnetic member 52 such that the third magnetic member 56 will travel from its retracted position to its extended position).

The holding portions 70c, 72c prohibit the second and third magnetic members 54, 56 from leaving their respective first, retracted positions (See, e.g. FIG. 4A) until the firing members 70, 72 are depressed or otherwise actuated by the operator. In other words, the holding portions 70c, 72c act as stoppers which physically counteract the magnetic forces applied to the second and third magnetic members 54, 56, thereby: (a) preventing the second magnetic member 54 from moving from its first extended position toward the first magnetic member 52, and (b) preventing the third magnetic member 56 from moving from its first retracted position away from the first magnetic member 52.

The interaction between the firing members 70, 72 and magnetic members 54 and 56 will now be discussed. With the second magnetic member 54 in its first retracted position (FIG. 3A, 4A), the first firing member 70 is biased in its holding position so that its holding member 70c engages a portion of a distal face of the second magnetic member 54 to effectively maintain the second magnetic member 54 in its first retracted position. And when the manually engageable portion 70d of the first firing member 70 is depressed, the first firing member 70 moves toward its firing position (FIG. 4B) and its holding member 70c disengages from the second magnetic member 54, allowing the second magnetic member 54 to automatically move toward the first magnetic member 52 (via magnetic attraction) to its second extended position (FIG. 4D). Further on, with the third magnetic member 56 is in its first, retracted position (FIG. 4A), the second firing member 72 is biased in its holding position so that its holding member 72c engages a portion of a distal face of the third magnetic member 56 to maintain the third magnetic member in its first, retracted position. And when the manually engageable portion 72d of the second firing member 72 is depressed, the second firing member 72 moves toward its firing position (FIG. 4C) and its holding member 72c disengages from the third magnetic member 56, allowing the third magnetic member 56 to move away from the first magnetic member 52 (via magnetic repulsion) to its second extended position (FIG. 4D).

Figure 5A:
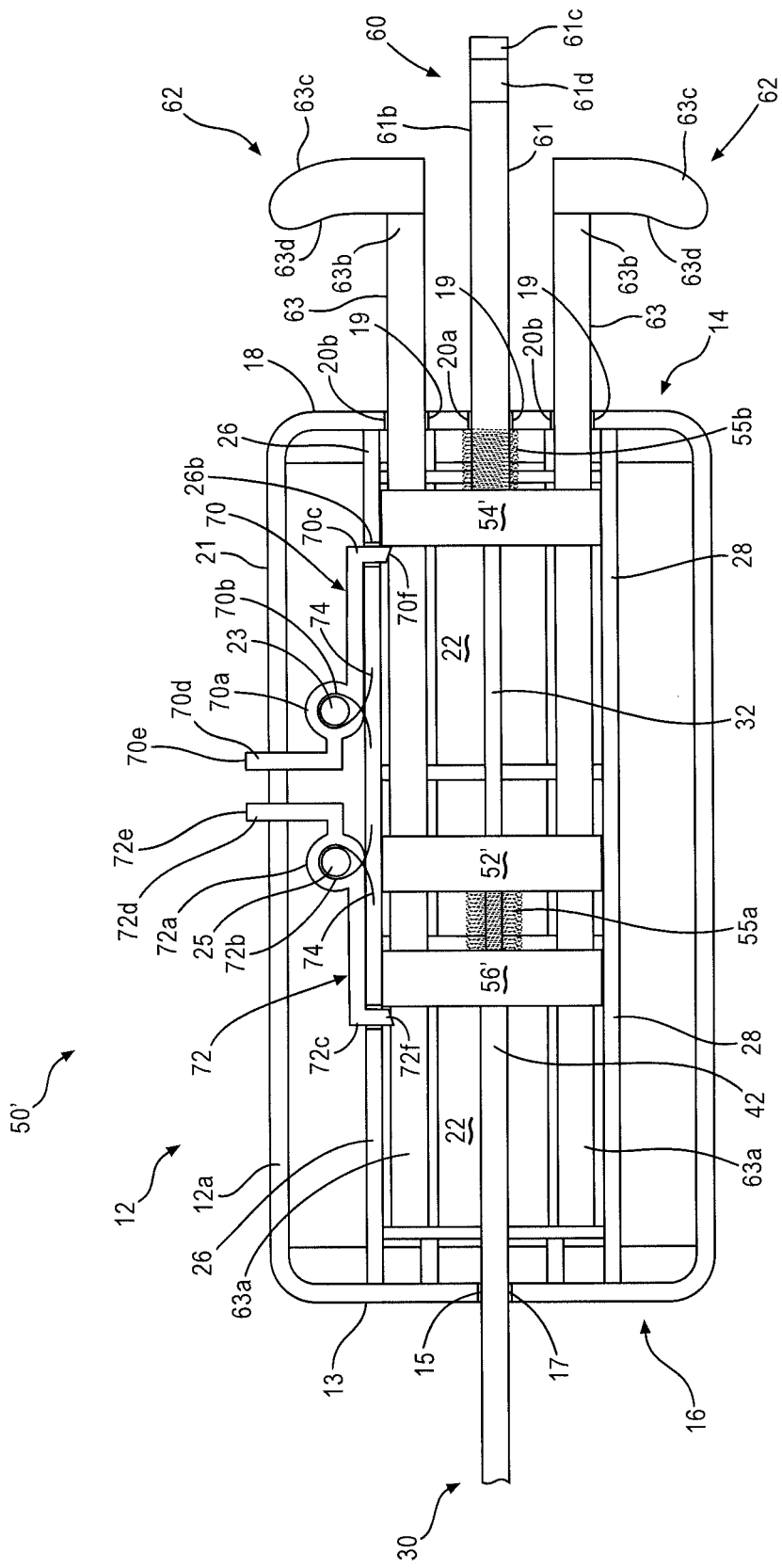
FIG. 5A is an enlarged sectional view of the housing and an alternative actuator mechanism, with the device in the retracted position.
Figure 5B:
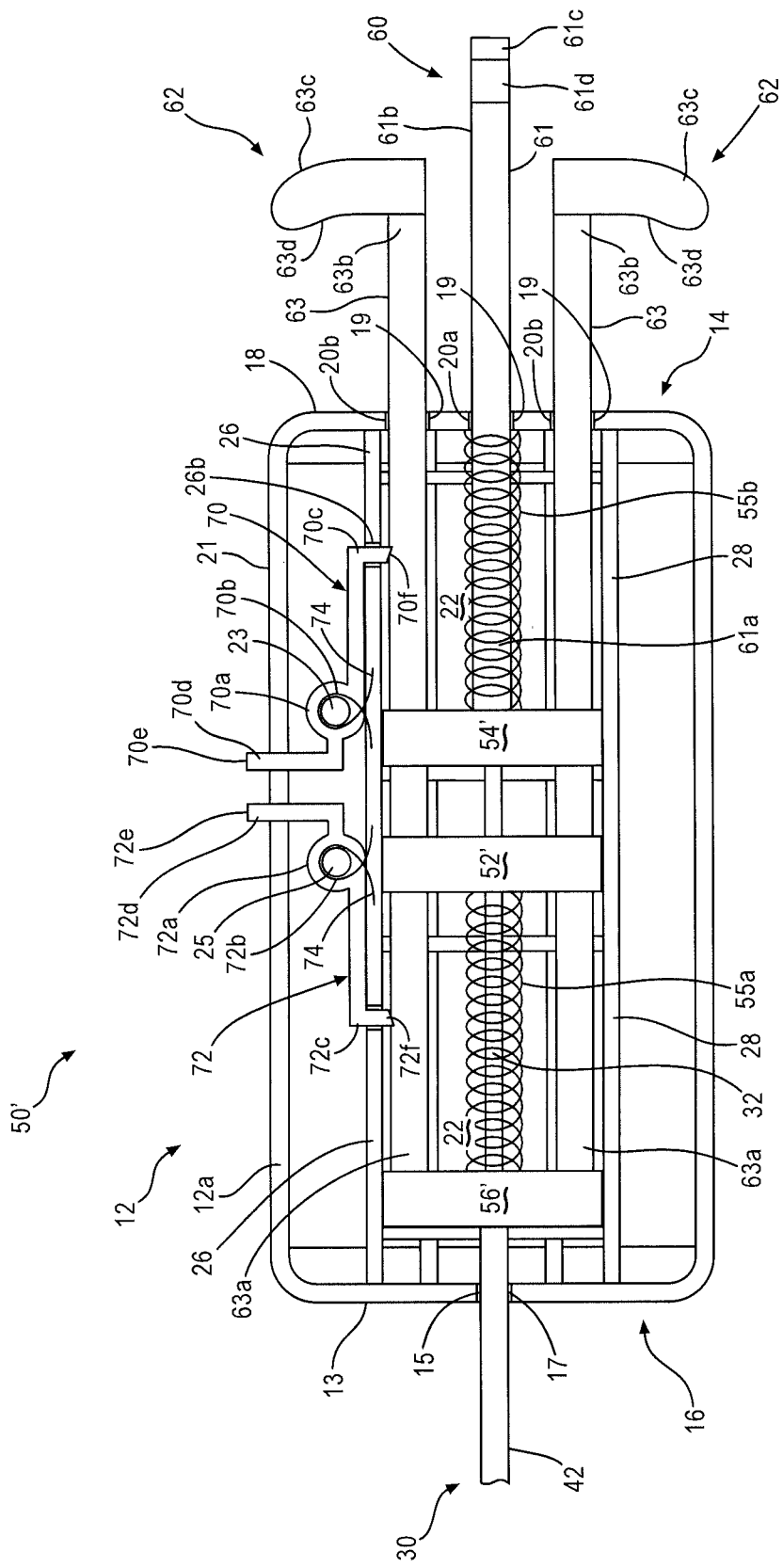
FIG. 5B is an enlarged sectional view of the housing an actuator mechanism of FIG. 5A, with the device in a fully fired position.

Referring now to FIGS. 5A-5B, an alternative arrangement of an actuator mechanism 50' is illustrated. Actuator mechanism 50' includes many of the identical components that have been described in connection with FIGS. 3A-3C and 4A-4D. Accordingly, for ease of explanation, those components have been given identical reference numbers.

Actuator mechanism 50' comprises two magnetic members to move one of the needle 32 or the cutting element 42 and a spring element 55a or 55b to move the other of the needle and the cutting element 42. In one exemplar arrangement, first and second magnetic elements 52' and 54' are provided as part of actuator mechanism 50' that correspond to the first and second magnetic elements 52 and 54 described above. However, third magnetic element is replaced by a non-magnetic plate 56' and spring element 55*a* is disposed between non-magnetic plate 56' and first magnetic member 52'. As may be seen in FIG. 5A, when the needle 32 and cutting element 42 are each in the first retracted position, first firing member 70 restrains the second magnetic member 54' in the first (retracted) position and second firing member 72 restrains the non-magnetic member 56' in the first (retracted) position. Further, when the non-magnetic member 56' is in the first (retracted) position, spring element 55*a* is compressed between the non-magnetic member 56' and the first magnetic member 52'.

In operation, when outboard end 70*e* is actuated, holding portion 70*c* is lifted so as to release the second magnetic member 54' from its first position. As described above, the magnetic attraction between first and second magnetic members 52' and 54' cause second magnetic member 54' to move in the first (distal) direction, as shown in FIG. 5B. And, because the needle 32 is fixed to the second magnetic member 54', the needle 32 is fired in the first distal direction when the second magnetic member 54' is moved toward the first magnetic member 52'.

When the outboard end 72*e* is actuated, the holding portion 72*c* is lifted so as to release the non-magnetic member 56' from its first position. The spring element 55*a*, which is trapped between the stationary first magnetic member 52' and the non-magnetic member 56', biases the non-magnetic member 56' in the first, distal direction, as shown in FIG. 5B. Because the cutting element 42 is fixed to the non-magnetic member 56', the cutting element 42 is fired in the first distal direction when the non-magnetic member 56' is released from the first retracted position.

It is also contemplated that second element 54' may be provided as a non-magnetic element and that spring element 55*b* is positioned between second non-magnetic element 54' and the proximal wall 18 of the housing 12. In this configuration, when outboard end 70*e* is actuated and holding portion 70*c* is lifted, second non-magnetic element 54' is released from its first position. The spring element 55*b* then biases the second non-magnetic element 54' in the first (distal) direction, as shown in FIG. 5B.

Finally, it is also understood that elements 52', 54', and 56' may all be configured as non-magnetic members and device 10 may be provided with two spring elements 55*a* and 55*b*. In this configuration, when the first and second firing members 70 and 72 are actuated, the second and third elements 54', 56' are released from the retracted position and the spring elements 55*a* and 55*b* bias the second and third elements 54', 56' in the first, distal direction.

Having thus described the biopsy device 10 and its components, attention will now be drawn to FIGS. 6-10 whereby a method of using the device to perform a needle biopsy to harvest tissue samples will now be described. To begin with, the device 10 is first placed in its retracted position, prior to insertion. More specifically, if the needle 32 and cutting element 42 are in the second extended/fired position, the actuator members 60, 62 are pulled in the second proximal direction relative to the housing 12. Pulling actuator members 60, 62 in such a manner moves second and third magnetic members 54, 56 (or non-magnetic members 54', 56', as described above), to which the needle 32 and cutting element 42 are attached, to the retracted position. More specifically, the operator grasps or otherwise engages the first manually engageable actuator member 60, pulling the actuator member 60 in the proximal direction relative to the housing 12. This movement causes the second magnetic member 54 to be pulled away from the first magnetic member 52 as it moves from its second position (See, e.g. FIG. 3C) toward its first position (See, e.g. FIG. 3A), which in turn causes the needle 32 to likewise move from its extended/fired position toward its retracted position. As the second magnetic member passes the first firing member 70, the holding portion 70*c* moves upward through the slot 26*a* in the upper support member 26 allowing the second magnetic member 54 to pass. Upon clearing the first firing member 70, the holding portion 70*c* moves downward through the slot 26*a* in the upper support member 22 and the first firing member 70 is biased into its holding position (See, e.g. FIG. 5), thus engaging and securing the second magnetic member 54 in its first retracted position and the needle 32 in its retracted (armed) position. Next, the user grasps or otherwise engages the second manually engageable actuator member 62, pulling the member 62 in the proximal direction relative to the housing 12. This movement causes the third magnetic member 56 to be pulled toward the first magnetic member 52 as it moves from its second (extended) position (See, e.g. FIG. 3C) toward its first (retracted) position (See, e.g. FIG. 3A), which in turn causes the cutting member 42 to move from its extended position toward its retracted position. As the third magnetic member 56 passes the second firing member 72, the holding portion 72*c* moves upward through the slot 26*a* in the upper support member 26 allowing the third magnetic member to pass. Upon clearing the second firing member 72, the holding portion 72*c* moves downward through the slot 26*a* in the upper support member 22 and the second firing member 72 is biased into its holding position (See, e.g. FIG. 6), thus engaging and securing the third magnetic member 56 in its first position and the cutting element 42 in its retracted (armed) position. In the above example the needle 32 is retracted first followed by the cutting element 42; however, it should be noted that the cutting element 42 could be retracted prior to the needle 32 if desired.

Figure 6:
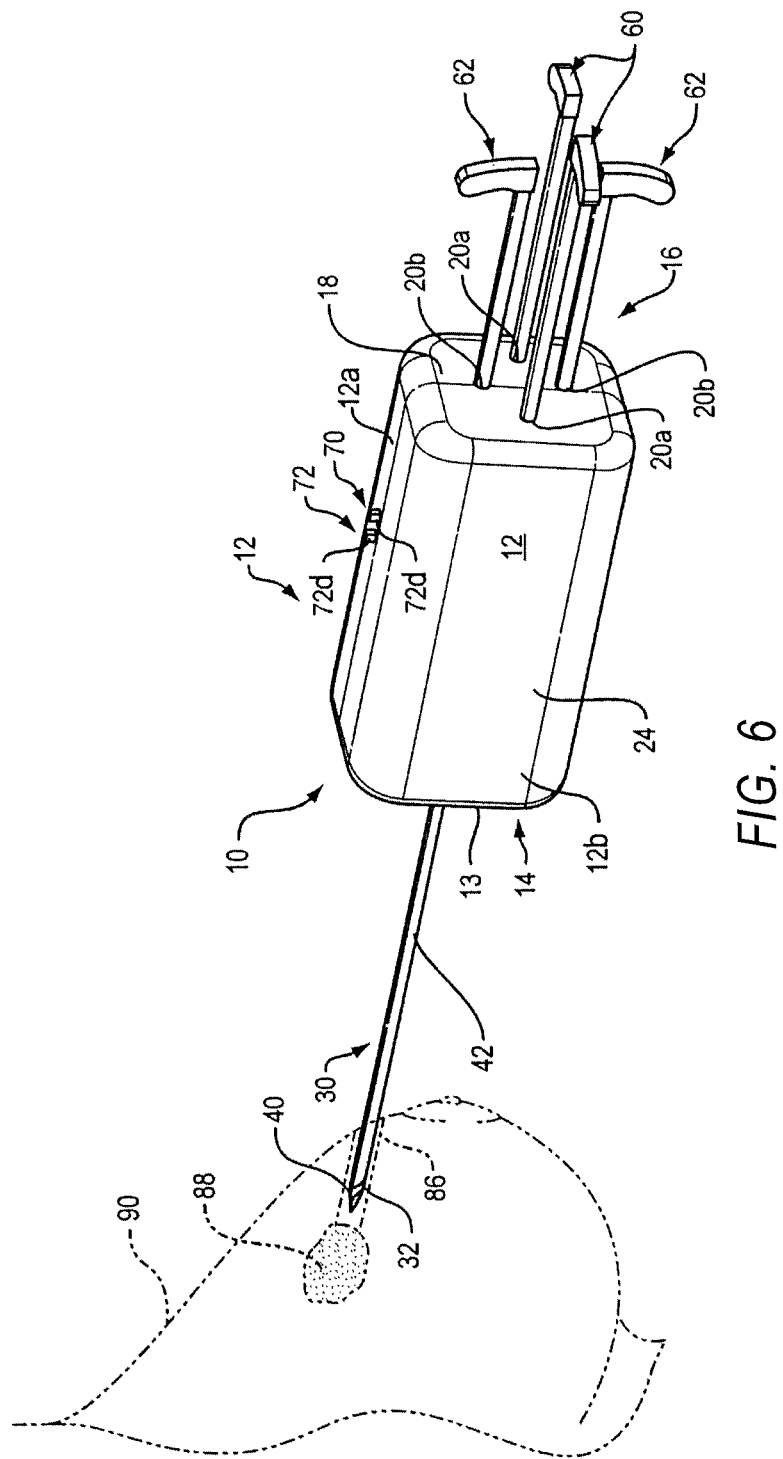
FIG. 6 is a perspective view showing the device of FIG. 1 being introduced to a target tissue site in a female breast with the device in the retracted position.

Having armed the device 10, the needle set 30 is ready to be introduced to a predetermined target tissue site 80 as illustrated, for example, in FIG. 6. By way of example only, the target tissue site 88 is shown in a female breast, however as one skilled in the art will appreciate, the device 10 can be used to perform biopsies or otherwise harvest tissue samples in other locations of the human body (male or female). Typically, the needle set 30 is introduced to the target site 88 under the guidance of an imaging modality (e.g. MRI, ultrasound, x-ray, tomography, nuclear medicine) and may be inserted through a previously formed tissue pathway 86 or through a previously implanted introducer sheath as will be described below. However, it is also understood that in embodiments where the needle 32 includes a tissue-piercing tip 40, it is further contemplated that the needle set 30 could be directly inserted into a patient's tissue to create its own tissue pathway without further assistance.

Figure 7:
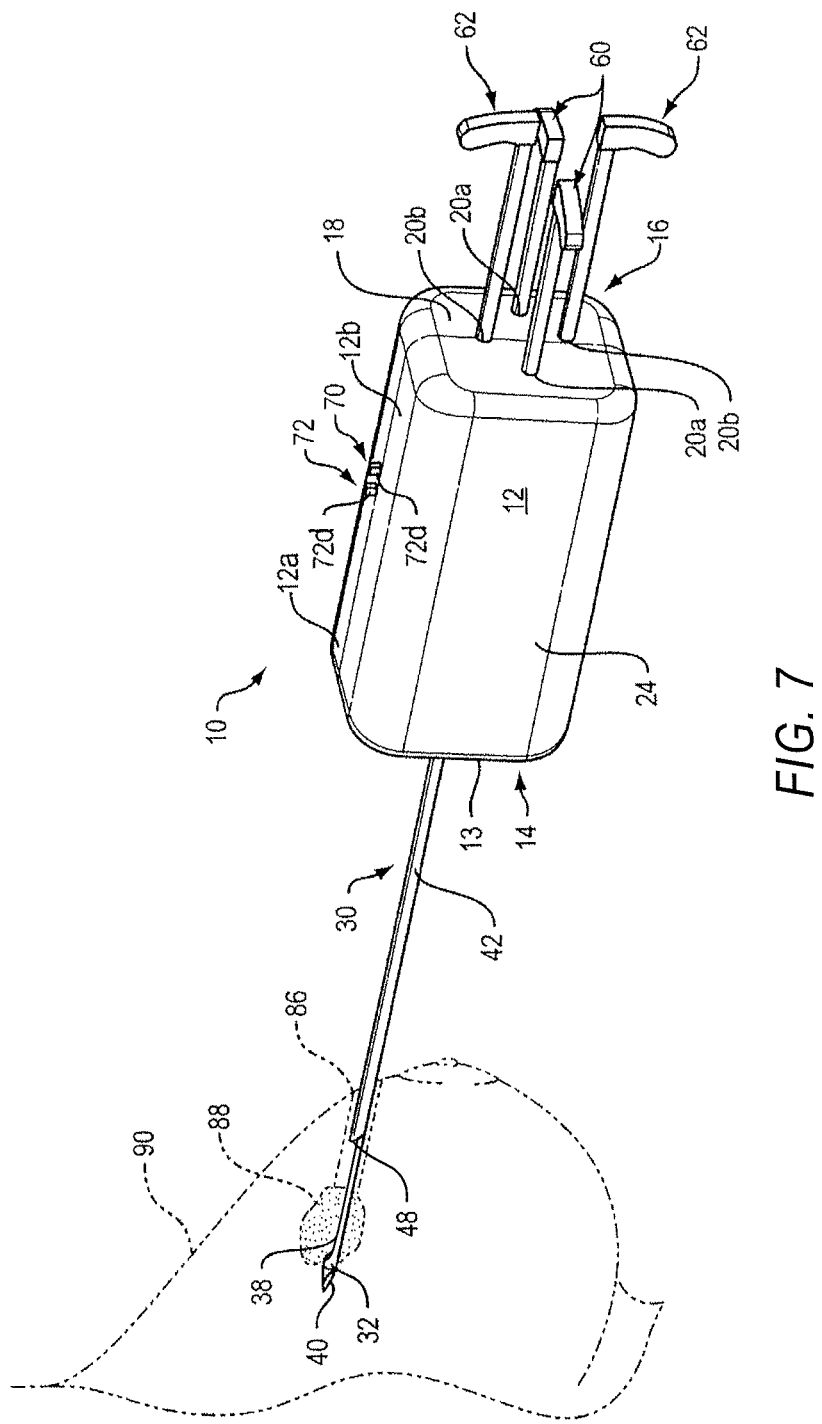
FIG. 7 is a perspective view of the device of FIG. 6 after a needle had been fired through the target tissue mass, but with a cutting element still remaining in the retracted position.
Figure 8:
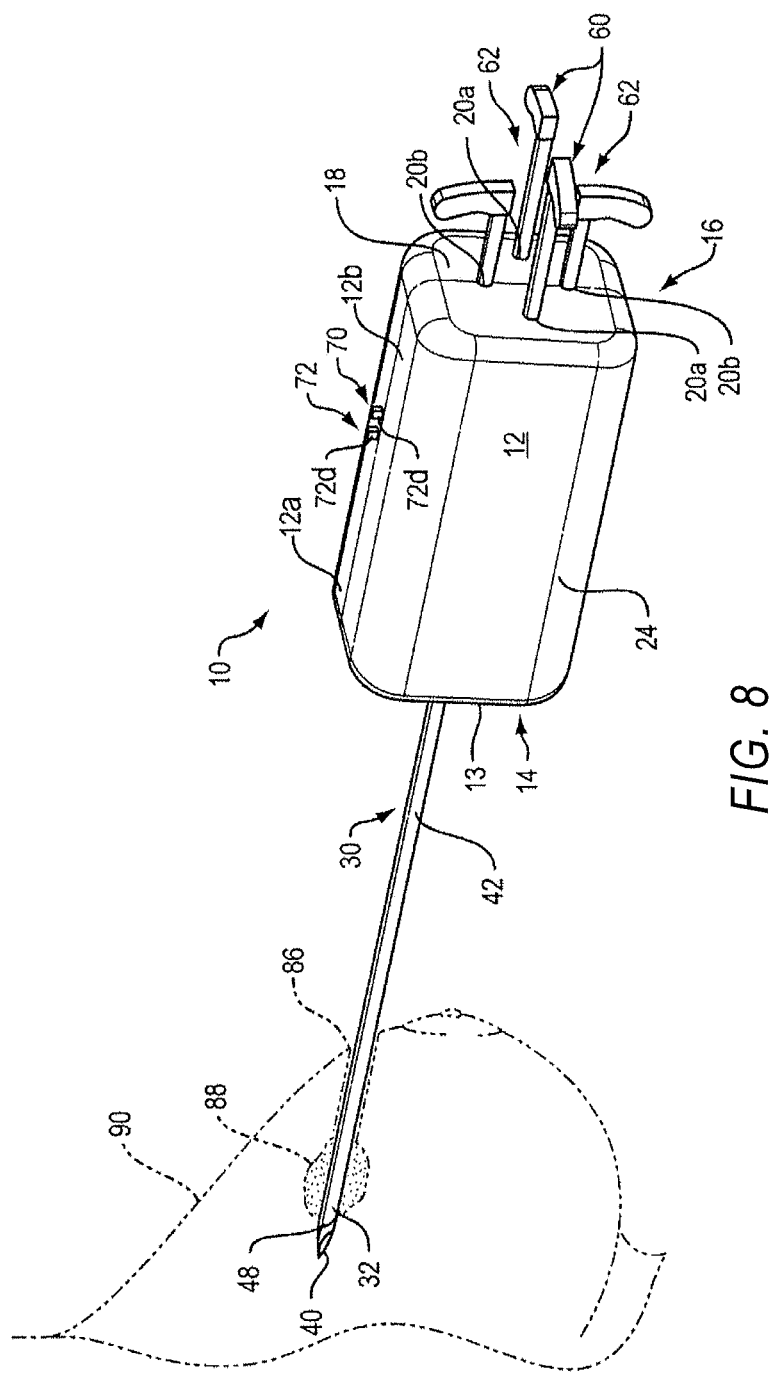
FIG. 8 is a perspective view of the device of FIG. 7 after the cutting element has been fired such that the device is in its fully fired position.

Once the needle set 30 is in the desired position relative to the target tissue site 88, the needle 32 is first fired into the tissue or lesion of interest thereby exposing the tissue receiving opening 38 to the tissue or lesion as shown, for example, in FIG. 7. To fire the needle 32, the operator depressed the manually engageable portion 70*d* of the first firing member 70 which caused the first firing member 70 to move from its holding position to its firing position. As this movement occurs, the holding portion 70*c* moves upward through the slot 26*a* in the upper support member 22 causing the holding portion 70*c* to disengage from second magnetic member 54. Once the holding portion is disengaged, the second magnetic member 54 moves toward the first magnetic member 52 from its first retracted position toward its second extended/fired position, the movement facilitated by the magnetic attraction forces between the first and second magnetic members 52 and 54. For an embodiment that includes one or more spring elements 55a, 55b, and non-magnetic members 54' and 56', the movement is facilitated by the spring force generated by the spring elements 55a, 55b being released from the compressed configuration.

Because the second magnetic member 54 is coupled to the needle 32 as described above, as the second magnetic member moves from its first position to its second position, the needle 32 simultaneously or substantially simultaneously is driven distally into the tissue or lesion from its retracted (armed) position to its extended (fired) position. With the needle 32 extended, the tissue receiving opening 38 is exposed (open), thus allowing tissue to prolapse or otherwise enter into the tissue receiving opening 38 (See, e.g. FIG. 7). If necessary, the operator can adjust the positioning of the tissue receiving opening 38 within the target site 88 to ensure that the desired segment of tissue is biopsied.

Once it is confirmed that the needle is placed and oriented at the desired location, the cutting member 42 is then fired distally (See, e.g. FIG. 8) to sever tissue and retrieve a biopsy sample or core. More specifically, to fire the cutting element 42, the operator depresses the manually engageable portion 72d of the second firing member 72 thereby causing the second firing member 72 to move from its holding position to its firing position. As this movement occurs, the holding portion 72c moves upward through the slot 26a in the upper support member 22 causing the holding portion 72c to disengage from third magnetic member 56. Once the holding portion 72c is disengaged, the third magnetic member 56 moves away from the first magnetic member 52 from its first retracted position toward its second position, the movement facilitated by the magnetic repulsion forces between the first and third magnetic members 52 and 56. Because the third magnetic member 56 is coupled to the cutting element 42 as described above, as the third magnetic member 56 moves from its first retracted position to its second fired position, the cutting element 42 simultaneously or substantially simultaneously is driven distally across the tissue receiving opening 38 as it moves from its retracted (armed) position to its extended (fired) position (See, e.g. FIG. 8). As the cutting element 42 moves across the tissue receiving opening 38, the cutting edge 48 severs tissue, separating the tissue residing in the tissue receiving opening 38 from the adjacent tissue, leaving a retrievable tissue sample or biopsy core in the tissue receiving opening 38.

Figure 9:
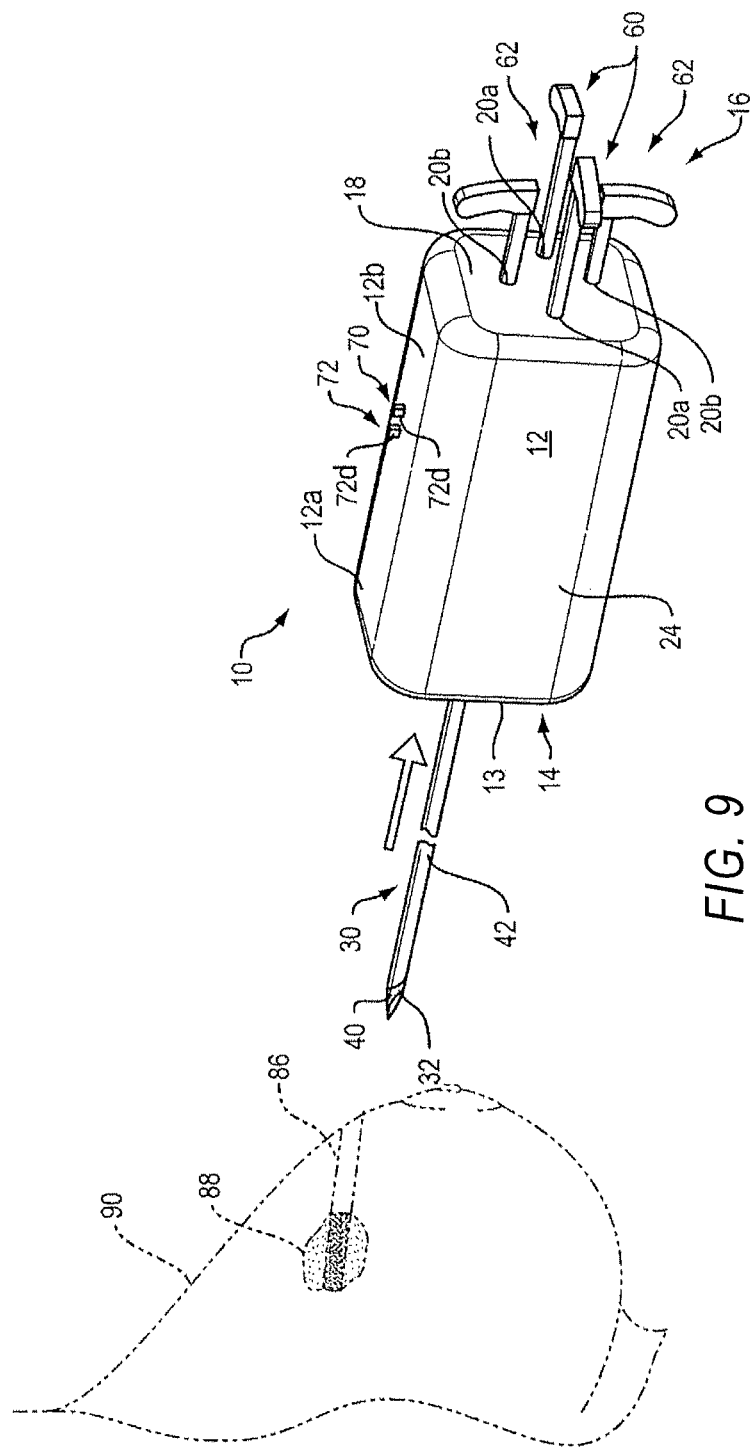
FIG. 9 is a perspective view of the device of FIG. 8 after the device has been removed from the breast and with a harvested tissue sample (not shown).
Figure 10:
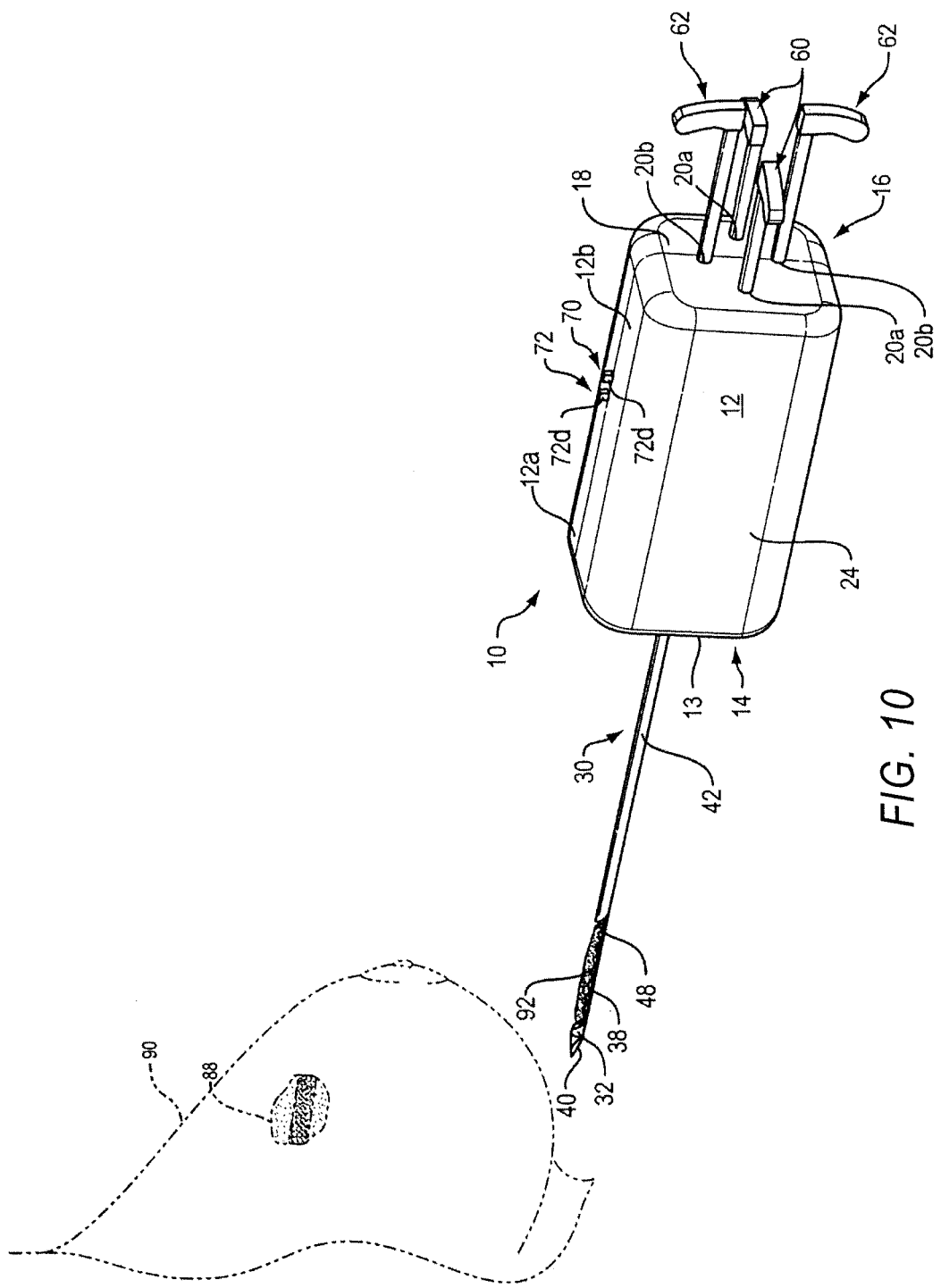
FIG. 10 is a perspective view of the device of FIG. 9 after the cutting element has been returned to the retracted position to exposing a tissue receiving aperture within the needle and the harvested tissue sample.
Figure 11:
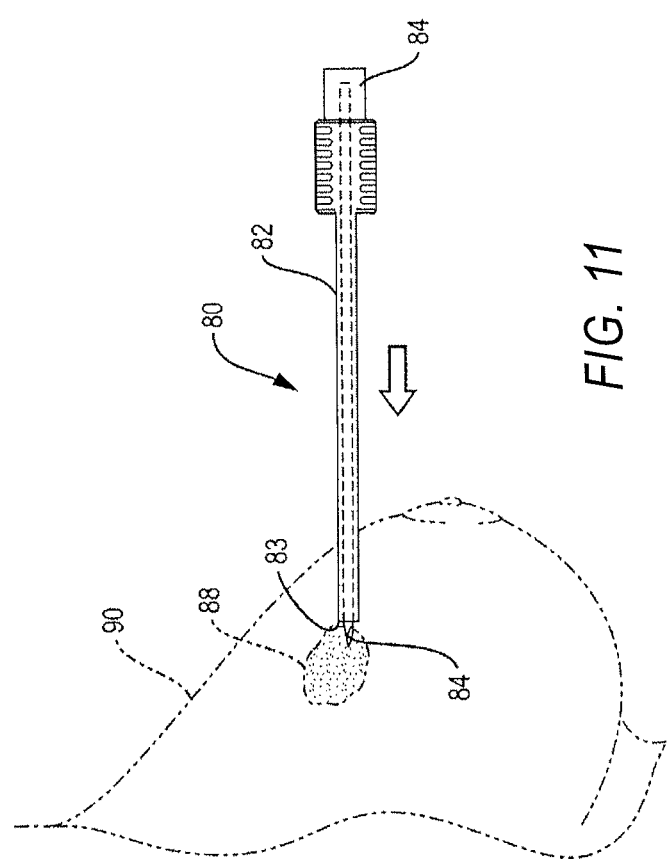
FIG. 11 is a side view of an embodiment of an introducer-stylet assembly usable in conjunction with the biopsy device of FIG. 1 to assist in introducing the device to a target tissue site.
Figure 12:
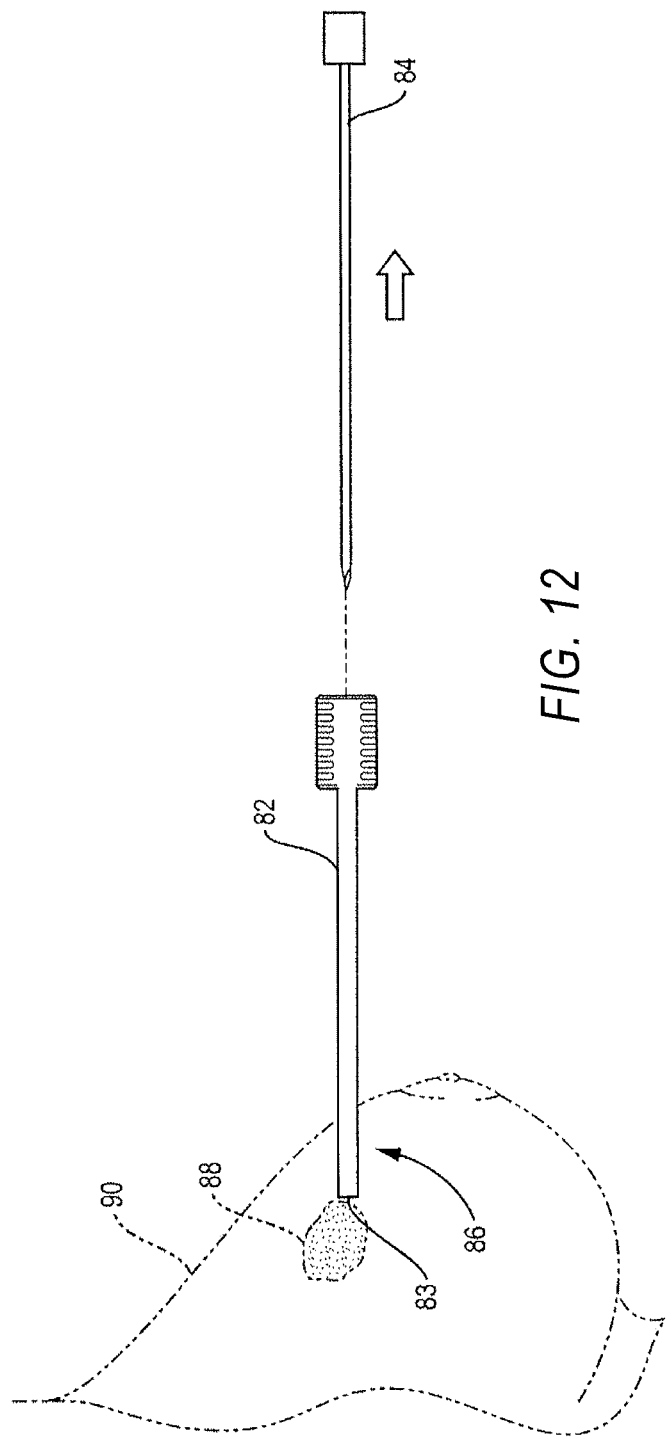
FIG. 12 is a side view of the introducer-stylet assembly of FIG. 11 with the stylet being retracted from the introducer sheath, but leaving the introducer sheath in the breast as a pathway leading to the target tissue site.

To retrieve the biopsy core or tissue sample, the operator removes the needle set 30 from the patient as shown, as shown, for example, in FIG. 9, and grasps or otherwise engages the second manually engageable actuator member 62, pulling the member 62 in the proximal direction relative to the housing 12. This movement causes the third magnetic member 56 to be pulled proximally toward the first magnetic member 52 as it returns from its second fired position toward its first retracted position, which in turn causes the cutting member 42 to move from its extended fired position toward its retracted position as shown, for example, in FIG. 10. As the third magnetic member 56 passes the second firing member 72, the holding portion 72c moves upward through the slot 26a in the upper support member 22 allowing the third magnetic member 56 to pass. Upon clearing the second firing member 72, the holding portion 72c moves downward through the slot 26a in the upper support member 22 and the second firing member 72 is biased into its holding position, thus engaging the third magnetic member 56 and securing said member in its first position and the cutting element 42 in its retracted position. With the cutting element 42 secured in its retracted position (See, e.g. FIG. 9), the tissue receiving opening 38 is once again exposed and the biopsy core 92 residing in the opening may be removed for analysis. If additional biopsy cores are desired, the operator then: moves the needle 32 from its extended fired position to its retracted (armed) position (as described above), reintroduces the needle set 30 into the patient to the target site, fires and positions the needle 32 (as described above), fires the cutting element 42 (as described above), removes the needle set 30 from the patient, and retracts the cutting element 42 (as described above) to expose the next biopsy core for retrieval and analysis. This procedure may be repeated until the desired number of cores have been obtained.

The biopsy device and needle set described herein can be provided in any suitable shape and size and can be manufactured using any suitable materials known to those of ordinary skill in the art. For example, to avoid interfering with the magnetic fields generated by the three magnetic members 52, 54, 56, in certain embodiments, the needle set 30 is composed of a substantially non-magnetic metallic material or alloy, including but not limited to 316 stainless steel, while the housing 12 and actuator assembly 50 and their respective features/components are primarily composed of substantially non-magnetic plastics or polymers, including but not limited to PP (polypropylene) and ABS (acrylonitrile butadiene styrene) plastics.

As illustrated in FIGS. 11-14, the biopsy device 10 may be used in conjunction with an introducer-stylet assembly 80. An introducer-stylet assembly 80 operates to effectively create a pathway leading to a desired target tissue site 88, through which the device 10 is inserted. An exemplary introducer-stylet assembly 80 includes an introducer sheath or cannula 82 defining a lumen or working channel 83 therethrough and a tissue-piercing stylet or trocar needle 84. In use, the tissue-piercing stylet 84 is first inserted into the introducer sheath 82. Next, the introducer-stylet assembly 80 is inserted into the patient under imaging guidance (e.g. MRI, ultrasound, x-ray, tomography, nuclear medicine) to a target tissue site 88, thereby creating the tissue pathway to the site 88. The stylet 84 is then removed, but the introducer sheath 82 is left in place relative to the target site 88. With the sheath 82 in place, the device 10 (particularly the needle set 30) is inserted into the working channel 83 of the sheath 82 until the distal end of the needle set 30 reaches the target site 88. At this point, the device 10 can be operated to retrieve the desired number of biopsy cores of tissue samples.

As may be recognized by those of ordinary skill in the pertinent art based on the teachings herein, numerous changes and modifications may be made to the above-described and other embodiments of the present disclosure without departing from the spirit and scope of the disclosure as defined and/or described in the specification, drawings and appended claims. It should be understood that the embodiments shown and described and all changes, modifications and equivalents that come within the spirit and scope of the disclosure are desired to be protected. Accordingly, this disclosure is to be taken in an illustrative, as opposed to a limiting sense.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary. Further, regarding the methods and processes described herein, it should be understood that although the steps of such methods and processes have been described as occurring according to a certain ordered sequence, such processes could be practiced with the described steps performed in an order other than the order described herein. It further should be understood that certain steps could be performed simultaneously, that other steps could be added, or that certain steps described herein could be omitted.

What is claimed is:

1. A biopsy device, comprising:
   a housing;
   a needle set mounted to the housing, the needle set comprising
      a needle defining proximal end, a distal end and a tissue-receiving opening, the needle movable relative to the housing; and
      a cutting element defining a proximal end, an open distal end and a cutting edge at the open distal end, the cutting element moveable relative to the housing, wherein the cutting element is configured to sever tissue projecting into the tissue-receiving opening; and
   an actuator assembly at least partially disposed in the housing, the actuator assembly comprising
      a first magnetic member fixed with respect to the housing, and
      second and third magnetic members movable with respect to the housing,
   wherein the second magnetic member is coupled to a first one of the needle and cutting element, and wherein the second magnetic member is magnetically attracted to the first magnetic member so as to move the first one of the needle or cutting element from a retracted position to an extended position, and
   wherein the third magnetic member is coupled to a second one of the needle and cutting element, and wherein the third magnetic member is repelled from the first magnetic member so as to move the second one of the needle or cutting element from a retracted position to an extended position.

2. The biopsy device of claim 1, the actuator assembly further comprising a manually engageable member that releasably engages the second magnetic member to thereby retain the first one of the needle and cutting element in a retracted position within the housing.

3. The biopsy device of claim 2, the actuator assembly further comprising a firing member movable between a holding position and a releasing position, wherein the firing member is configured such that, when the firing member is moved to the releasing position, the firing member releases the manually engageable member from the second magnetic member.

4. The biopsy device of claim 3, wherein the firing member is biased in the holding position.

5. The biopsy device of claim 2, wherein the second magnetic member is coupled to the needle such that when the manually engageable member is released from the second magnetic member, the needle moves from a retracted position to an extended position.

6. The biopsy device of claim 1, wherein the second magnetic member is proximally located in the housing relative to the first magnetic member.

7. The biopsy device of claim 1, wherein the needle includes a lumen in communication with the at least one tissue receiving opening and the cutting element includes a lumen, wherein the needle is slidably disposed coaxially within the lumen of the cutting element.

8. The biopsy device of claim 1, wherein the housing defines therein at least one support platform configured to maintain the second magnetic member on an axial pathway substantially parallel to a longitudinal axis of the needle set as the second magnetic member moves toward the first magnetic member.

9. The biopsy of device of claim 1, wherein the needle comprises one of a tissue piercing tip and a blunt tip at a distal end thereof.

10. The biopsy device of claim 1, the actuator further comprising first and second manually engageable members that releasably engage the second and third magnetic members to thereby retain the needle and cutting element in their respective retracted positions within the housing.

11. The biopsy device of claim 10, the actuator assembly further comprising first and second firing members movable between respective holding and releasing positions, wherein the first and second firing members are configured such that, when the first firing member is moved to the first firing member's releasing position, the first firing member releases the first manually engageable member from the second magnetic member, and when the second firing member is moved to the second firing member's releasing position, the second firing member releases the second manually engageable member from the third magnetic member.

12. The biopsy device of claim 1, further comprising first and second actuator members that are operatively connected to the second and third magnetic members, respectively, wherein the first actuator member is movable relative to the housing to move the second magnetic member away from the first magnetic member, and wherein the second actuator member is movable relative to the housing to move the third magnetic member towards the first magnetic member.

13. The biopsy device of claim 1, wherein the first, second and third magnetic members comprise magnets selected from the group consisting of: Neodymium magnets (NdFeB), Samarium-Cobalt magnets (SmCo), Alnico magnets (AlNiCo) and ceramic (ferrite) magnets.

14. A needle biopsy system device, comprising:
   a housing;
   a needle set mounted to the housing, the needle set comprising
      a needle defining a proximal end, a distal end and a tissue receiving opening, the needle movable between a retracted position and an extended position, and
      a cutting element defining a proximal end, a distal end and a cutting edge formed on the distal end, the cutting element moveable relative to the housing between a retracted position and an extended position, wherein the cutting element is configured to sever tissue projecting into the tissue-receiving opening when the cutting element is moved from the cutting element's retracted position to the cutting element's extended position;
   an actuator assembly at least partially disposed in the housing, the actuator assembly comprising
      a first magnetic member fixed with respect to the housing,
      a second magnetic member movable with respect to the housing, wherein the second magnetic member is magnetically attracted toward the first magnetic member, and wherein the second magnetic member is configured to move under the force of the magnetic attraction in a distal direction relative to the housing from a first position to a second position, and
      a third magnetic member movable with respect to the housing wherein the third magnetic member is magnetically repelled away from the first magnetic member, and wherein the third magnetic member is configured to move under the force of the magnetic repulsion in the distal direction relative to the housing from a first position to a second position; and first and second actuator members operatively connected to the second and third magnetic members, respectively, wherein the second magnetic member is coupled to the needle such that movement of the second magnetic member from the second magnetic member's first position to the second magnetic member's second position moves the coupled needle from the needle's retracted position to the needle's extended position, wherein the third magnetic member is coupled to the cutting element such that movement of the third magnetic member from the third magnetic member's first position to the third magnetic member's second position moves the coupled cutting element from cutting element's retracted position to cutting element's extended position, and wherein the first and second actuator members are independently movable in a proximal direction relative to the housing to move the second and third magnetic members to their respective first positions.

15. The biopsy device of claim 14, the actuator assembly further comprising a first firing member and a second firing member, each of the first and second firing members movable between a holding position and a releasing position, wherein the first firing member is configured such that moving the first firing member to the first firing member's releasing position releases the needle from the needle's retracted position, and wherein the second firing member is configured such that moving the second firing member to the second firing member's releasing position releases the cutting element from the cutting element's retracted position.

* * * * *